United States Patent
Kim et al.

(10) Patent No.: US 11,213,583 B2
(45) Date of Patent: Jan. 4, 2022

(54) METHODS AND COMPOSITIONS FOR TREATING CANCER AND INFECTIOUS DISEASES

(71) Applicant: Cedars-Sinai Medical Center, Los Angeles, CA (US)

(72) Inventors: Hyung Kim, Los Angeles, CA (US); Yanping Wang, Los Angeles, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 0 days.

(21) Appl. No.: 15/116,485

(22) PCT Filed: Feb. 5, 2015

(86) PCT No.: PCT/US2015/014687
§ 371 (c)(1),
(2) Date: Aug. 3, 2016

(87) PCT Pub. No.: WO2015/120198
PCT Pub. Date: Aug. 13, 2015

(65) Prior Publication Data
US 2017/0007698 A1 Jan. 12, 2017

Related U.S. Application Data

(60) Provisional application No. 61/936,168, filed on Feb. 5, 2014.

(51) Int. Cl.
| | |
|---|---|
| A61K 39/395 | (2006.01) |
| A61K 31/436 | (2006.01) |
| A61K 39/00 | (2006.01) |
| A61K 39/39 | (2006.01) |
| A61K 45/06 | (2006.01) |

(52) U.S. Cl.
CPC ........ *A61K 39/3955* (2013.01); *A61K 31/436* (2013.01); *A61K 39/0011* (2013.01); *A61K 39/39* (2013.01); *A61K 45/06* (2013.01); *A61K 2039/505* (2013.01); *A61K 2039/507* (2013.01); *A61K 2039/5154* (2013.01); *A61K 2039/545* (2013.01); *A61K 2039/55544* (2013.01)

(58) Field of Classification Search
CPC .......... A61K 39/3955; A61K 2039/505; A61K 2039/507; A61K 2039/5154; A61K 2039/545; A61K 2039/5544
See application file for complete search history.

(56) References Cited

U.S. PATENT DOCUMENTS

| | | | |
|---|---|---|---|
| 8,906,374 B2 | 12/2014 | Kim et al. | |
| 9,427,463 B2 | 8/2016 | Kim et al. | |
| 10,039,825 B2 | 8/2018 | Kim et al. | |
| 2006/0051357 A1 | 3/2006 | Katopodis et al. | |
| 2008/0031882 A1 | 2/2008 | Liang et al. | |
| 2008/0112888 A1 | 5/2008 | Wang | |
| 2009/0226430 A1 | 9/2009 | Hanna et al. | |
| 2009/0311249 A1 | 12/2009 | Gianni et al. | |
| 2009/0317407 A1* | 12/2009 | LaCelle | C07K 16/26 424/174.1 |
| 2010/0055102 A1* | 3/2010 | Langermann | A61K 31/675 424/134.1 |
| 2010/0196311 A1 | 8/2010 | Kim et al. | |
| 2010/0310573 A1* | 12/2010 | Nakagawa | C07K 16/2812 424/144.1 |
| 2013/0028898 A1* | 1/2013 | Kim | A61K 31/436 424/135.1 |
| 2015/0064180 A1 | 3/2015 | Kim et al. | |
| 2017/0021016 A1 | 1/2017 | Kim et al. | |
| 2017/0328887 A1 | 11/2017 | Matsushima et al. | |
| 2019/0015504 A1 | 1/2019 | Kim et al. | |

FOREIGN PATENT DOCUMENTS

| | | | |
|---|---|---|---|
| CA | 2937035 A1 | 8/2015 | |
| CN | 105979961 A1 | 9/2016 | |
| EP | 3102233 A1 | 12/2016 | |
| IN | 201617026443 A | 8/2016 | |
| JP | 2017507931 A1 | 3/2017 | |
| WO | 199701002 A1 | 3/1997 | |
| WO | 2004045512 A2 | 6/2004 | |
| WO | 2006050172 A2 | 5/2006 | |
| WO | 2007130555 A2 | 2/2007 | |
| WO | 2010124498 A1 | 3/2010 | |
| WO | 2010/124498 A1 | 11/2010 | |

(Continued)

OTHER PUBLICATIONS

Cancer information from National Institute of Cancer, Apr. 29, 2010, pp. 1-2. (Year: 2010).*
Mkrtichyan et al., Eur. J. Immunol. 2011, 41:2977-2986. (Year: 2011).*
PCT/US2015/014687 International Preliminary Report on Patentability dated Aug. 18, 2016; 7 pages.
PCT/US2011/033191 International Search Report and Written Opinion dated Jun. 29, 2011; 7 pages.
PCT/US2011/033191 International Preliminary Report on Patentability dated Oct. 23, 2012; 6 pages.

(Continued)

*Primary Examiner* — Hong Sang
(74) *Attorney, Agent, or Firm* — Jun He Law Offices P.C.; James J. Zhu

(57) ABSTRACT

The invention relates to compositions comprising a CD4 lymphocyte depleting agent; and methods of using the compositions to treat, prevent, reduce the severity of and/or slow the progression of a condition in a subject. The invention also relates to use of combinations of a CD4 lymphocyte depleting agent and at least one additional agent to treat, prevent, reduce the severity of and/or slow the progression of a condition in a subject. The additional agent may be an immune check point inhibitor, an adoptive immune therapeutic, an immune adjuvant, or an immune modulating agent, or their combinations.

18 Claims, 22 Drawing Sheets

(56) References Cited

FOREIGN PATENT DOCUMENTS

| WO | WO-2011109789 A2 * | 9/2011 | ......... C07K 16/2812 |
|---|---|---|---|
| WO | 2011133636 A1 | 10/2011 | |
| WO | WO-2011139738 A2 * | 11/2011 | ......... A61K 38/2013 |
| WO | 2013/043647 A1 | 3/2013 | |
| WO | 2015120198 A1 | 8/2015 | |

OTHER PUBLICATIONS

PCT/US2015/014687 International Search Report and Written Opinion dated Apr. 21, 2015; 8 pages.
Marzec et al. IL-2-and IL-15-induced activation of the rapamycin-sensitive mTORC1 pathway in malignatnt CD4+ T lymphocytes. Blood (2008).111:2181-89.
Rider et al. A Human CD4 Monoclonal Antibody for the Treatment of T-Cell Lymphoma Combines Inhibition of T-Cell Signaling by a Dual Mechanism with Potent Fc-Dependent Effector Activity. Cancer Res. (2007). 67(2):9945-53.
Kataja et al. Primary breast cancer: ESMO Clinical Recommendations for diagnosis, treatment and follow-up. Ann Oncol (2009). 20(Supplemental 4): iv 10-14.
Balmana et al. BRCA in breast cancer: ESMO Clinical Recommendations. Ann Oncol (2009). 20(Supplemental 4): iv 19-20.
Nelson et al. Screening for Breast Cancer: An Update for the U.S. Preventive Services Task Force. Ann Intern Med (2009).151:727-737.
Li et al. CD8+ T-Cell Depletion and Rapamycin Synergize with Combined Coreceptor/Stimulation Blockade to Induce Robust Limb Allograft Tolerance in Mice. Am J Transplant (2008). 8:2527-2536.
Restifo et al. Adoptive immunotherapy for cancer: harnessing the T cell response. Nature Reviews (2012). 12:269-281.
Saroj et al. An overview on Immunomodulation. Journal of Advanced Scientific Research (2012). 3(1):7-12.
Toka et al. CD4+ CD25+ T Cells Regulate Vaccine-Generated Primary and Memory CD8+ T-Cell Responses against Herpes Simplex Virus Type 1. J Virol (2004). 78(23): 13082-13089.
Morse et al. Depletion of human regulatory T cells specifically enhances antigen-specific immune responses to cancer vaccines. Blood (2008). 112:610-618.
Jing et al. Depletion of CD4 T cells enhances immunotherapy for neuroblastoma after syngeneic HSCT but compromises development of antitumor immune memory. Blood (2009). 113(18):4449-4457.
Radvanyi et al. Antagonist Antibodies to PD-1 and B7-H1 (PD-L1)in the Treatment of Advanced Human Cancer-Letter. Clin Cancer Res (2013). 19(19): 2 pages.
Goding et al. Restoring immune function of tumor-specific CD4+ T cells during recurrence of melanoma. J Immunol (2013). 090(9):4899-4909.
European Search Report for EP15747022.0 dated Oct. 25, 2017, 24 pages.
Madeleine Devic, Systemic Monotherapy vs. Combination Therapy for CTCL: Rationale and Future Strategies, Cancer Network, Oncology Journal, 2007, vol. 21, 5 pages.
Partial Search Report for EP15747022.0 dated Aug. 7, 2017, 15 pages.
Arora et al., Effect of CD4-Depleting Antibody on the Development of *Cryptococcus* Neoformans-Induced Allergic Bronchopulmonary Mycosis in Mice, Infection and Immunity, 2006, vol. 74(7), pp. 4339-4348.
Kim et al., Clinical Efficacy of Zanolimumab (HuMax-CD4): Two Phase 2 Studies in Refractory Cutaneous T-Cell Lymphoma, Blood, 2007, vol. 109(11), pp. 4655-4622.
Notice of Reasons for Rejection of Japanese Patent Application No. 2016-550261, dated Oct. 22, 2018, 12 Pages.
Choi et al., Mechanisms Involved in Synergistic Anticancer Immunity of Anti-4-1BB and Anti-CD4 Therapy, 2007, Cancer Res., vol. 67(18), pp. 8891-8899.

Teng et al., Multiple Antitumor Mechanisms Downstream of Prophylactic Regulatory T-Cell Depletion, 2010, Cancer Res., vol. 70(7), pp. 2665-2674.
Alan G. Ramsay, Immune Checkpoint Blockade Immunotherapy to Activate Anti-Tumour T-Cell Immunity, 2013, British J. of Haematoloty, vol. 162, pp. 313-325.
Ruuls et al., Novel Human Antibody Therapeutics: The Age of the Umabs, 2008, Biotechnol. J., vol. 3, pp. 1157-1171.
Fukui et al.. Anti-tumor activity of dendritic cells transfected with mRNA for receptor for hyaluronan-mediated motility is mediated by CD4+ T cells, 2006, Cancer Immunol. Immunother, vol. 55, pp. 538-546.
Llewellyn-Smith et al., Effects of anti-CD4 antibody treatment on lymphocyte subsets and stimulated tumor necrosis factor a production: a study of 29 multiple sclerosis patients entered into a clinical trial of cM-T412, 1997, Neurology, vol. 48, pp. 810-816. Abstract only, 2 Pages.
Rep et al., Treatment with depleting CD4 monoclonal antibody results in a preferential loss of circulating naive T cells but does not affect IFN-g secreting TH1 cells in humans, 1997, J. Clin Invest., vol. 99, pp. 2225-2231.
Van der Lubbe et al., Treatment with a chimeric CD4 monoclonal antibody is associated with a relative loss of CD4 þ /CD45RA þ cells in patients with rheumatoid arthritis, 1997, J. Autoimmun., vol. 10(1), pp. 87-97. Abstract only, 2 Pages.
Wang et al., Foxp3+ T Cells Inhibit Antitumor Immune Memory Modulated by mTOR Inhibition, 2014, Cancer Research, vol. 74(8), 13 Pages.
Zeng Jing et al: "Anti-PD-1 Blockade and Stereotactic Radiation Produce Long-Term Survival in Mice With Intracranial Gliomas", International Journal of Radiation: Oncology Biology Physics, Pergamon Press, USA,vol. 86, No. 2, Feb. 22, 2013 (Feb. 22, 2013), pp. 343-349, XP028531184, ISSN: 0360-3016, DOI: 10.1016/J.IJROBP.2012.12.025.
P Penaloza-Macmaster et al: "Severely exhausted CD8 T cells are refractory to rescue by PD-1 blockade, but re-invigorate following concomitant CD4 T cell depletion in vivo (P6097)", J Immunol, Jan. 1, 2013 (Jan. 1, 2013), XP55610809, [retrieved on Aug. 5, 2019].
K. Takeda et al: "Combination Therapy of Established Tumors by Antibodies Targeting Immune Activating and Suppressing Molecules",The Journal of Immunology, vol. 184, No. 10, Apr. 16, 2010 (Apr. 16, 2010), pp. 5493-5501, XP055123621,ISSN: 0022-1767, DOI: 10.4049/jimmunol.0903033.
Annemieke Th. Den Boer et al: "CD4+ T Cells Are Able to Promote Tumor Growth through Inhibition of Tumor-Specific CD8+ T-Cell Responses in Tumor-Bearing Hosts", Cancer Research, Aug. 1, 2005 (Aug. 1, 2005), pp. 6984-6989, XP55610713,United States, DOI: 10.1158/0008-5472.CAN-04-3344, Retrieved from the Internet:URL :http://cancerres.aacrjournals.org/content/65/15/6984.full-text.pdf.
Croce, M. et al.,"Transient depletion of CD4+ T cells augments IL-21-based immunotherapy of disseminated neuroblastoma in syngeneic mice", International Journal of Cancer (2009), vol. 127, pp. 1141-1150.
Jacobs, J. F. M. et al.,"Dendritic Cell Vaccination in Combination with Anti-CD25 Monoclonal Antibody Treatment: A Phase I/II Study in Metastatic Melanoma Patients", Clinical Cancer Research (2010), vol. 16(20), pp. 5067-5078.
Zhang, B. et al.,"Depletion of Regulatory T Cells Facilitates Growth of Established Tumors: A Mechanism Involving the Regulation of Myeloid-Derived Suppressor Cells by Lipoxin A 4", The Journal of Immunology (Dec. 2010), vol. 185, pp. 7199-7206.
Ueha, S. et al.,"Robust Antitumor Effects of Combined Anti-CD4-Depleting Antibody and Anti-PD-1/PD-L1 Immune Checkpoint Antibody Treatment in Mice", Cancer Immunology Research (Jun. 2015), vol. 3(6), pp. 631-640.
The Second Office Action in Chinese Patent Application No. 201580007415.4, dated Sep. 16, 2019.
The Office Action in European Patent Application No. 15747022.0, dated Aug. 9, 2019.
The translation of the Notice of Reasons for Rejection in Japanese Patent Application No. 2016-550261, dated Jun. 17, 2019.

(56) References Cited

OTHER PUBLICATIONS

First Office Action issued by from the Indian Patent Office dated Oct. 14, 2020.

* cited by examiner

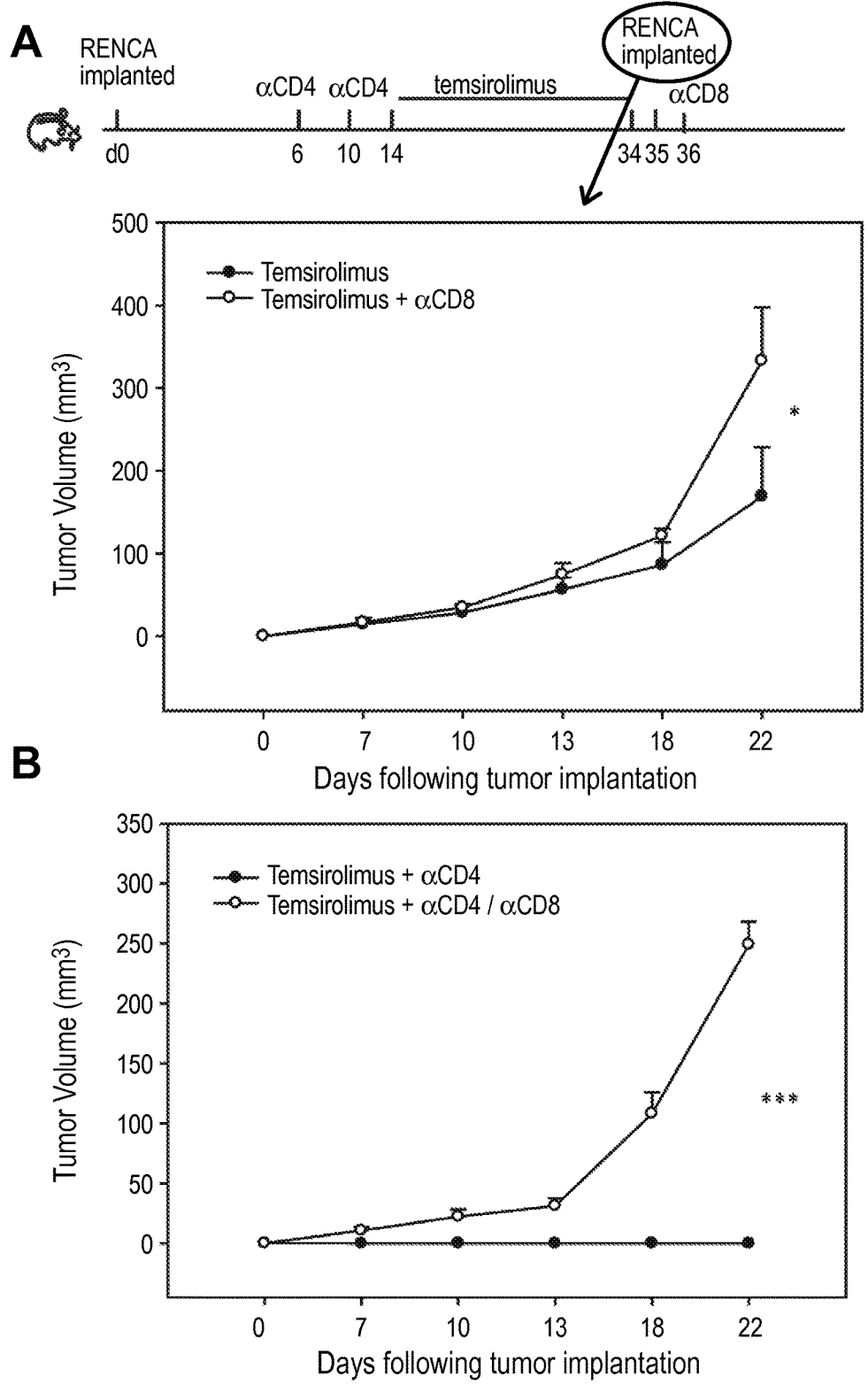

A

B

A

A

B

METHODS AND COMPOSITIONS FOR TREATING CANCER AND INFECTIOUS DISEASES

CROSS-REFERENCE TO RELATED APPLICATIONS

This application is a National Phase of International Application No. PCT/US2015/014687 filed Feb. 5, 2015, currently pending, which designated the U.S. and that International Application was published under PCT Article 21(2) in English, which also includes a claim of priority under 35 U.S.C. § 119(e) to U.S. provisional patent application No. 61/936,168 filed Feb. 5, 2014, now expired, the entirety of which is hereby incorporated by reference.

FIELD OF THE INVENTION

The present invention relates to molecular immunology and cell biology. Specifically described herein are compositions and methods for treating cancer or infectious diseases using CD4 lymphocyte depleting agents alone or in a combination with any one or more of an immune check point inhibitor, an adoptive immune therapeutic, an immune adjuvant, or an immune modulating agent.

BACKGROUND

All publications cited herein are incorporated by reference in their entirety to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

The immune system can provide protection against cancers. Effective immune stimulation produces long-lasting memory lymphocytes, capable of rapidly responding to repeat antigen challenge. CD4 expressing lymphocytes include both helper T cells and regulatory T cells. T helper cells are critical to mounting an adoptive immune response. However, regulatory T cells (Tregs) inhibit the function of cytotoxic T cells and normally function to limit an immune response. Therefore, CD4 depletion was evaluated as a strategy for removing Treg activity. Although only a small fraction of CD4 lymphocytes are Treg cells, CD4 depletion remains an effective approach for depleting Treg activity, and importantly, it has the potential for rapid translation to clinical use. Humanized CD4 depleting antibodies have been evaluated as a strategy to inhibit the immune system in clinical trials for autoimmune disorder. However, described herein is the use of CD4 lymphocyte depleting antibody to stimulate the immune system. Provided herein are therapies against cancer and infectious diseases in subjects by combining depletion of CD4+ lymphocytes with any one or more of an immune check point inhibitor, an adoptive immune therapeutic, an immune adjuvant, and an immune modulating agent, or a combination thereof.

SUMMARY OF THE INVENTION

Various embodiments of the present invention provide methods for treating, preventing, reducing the severity of and/or slowing the progression of a condition in a subject. The method includes providing a composition comprising a CD4 lymphocyte depleting agent and administering a therapeutically effective amount of the composition to the subject, thereby treating, preventing, reducing the severity of and/or slowing the progression of the condition in the subject.

Various embodiments of the present invention provide methods for treating, preventing, reducing the severity of and/or slowing the progression of a condition in a subject. The method includes providing a CD4 lymphocyte depleting agent and at least one additional agent selected from the group consisting of an immune check point inhibitor, an adoptive immune therapeutic, an immune adjuvant, and an immune modulating agent; and administering a therapeutically effective amount of the CD4 lymphocyte depleting agent and a therapeutically effective amount of the at least one of an immune check point inhibitor, an adoptive immune therapeutic, an immune adjuvant, and an immune modulating agent to the subject, thereby treating, preventing, reducing the severity of and/or slowing the progression of the condition in the subject. In some embodiments, the methods further comprise administering a therapeutically effective amount of mTOR inhibitor.

Various embodiments of the present invention provide methods for treating, preventing, reducing the severity of and/or slowing the progression of a condition in a subject. The methods include providing a CD4 lymphocyte depleting agent and an adoptive immune therapeutic agent (for example, a dendritic cell (DC) vaccine) and administering a therapeutically effective amount of the CD4 lymphocyte depleting agent and a therapeutically effective amount of the adoptive immune therapeutic agent thereby treating, preventing, reducing the severity of and/or slowing the progression of the condition in the subject.

Various embodiments of the present invention provide methods for treating, preventing, reducing the severity of and/or slowing the progression of a condition in a subject. The methods include providing a CD4 lymphocyte depleting agent and a checkpoint inhibitor (for example, an anti-PD-1 antibody) and administering a therapeutically effective amount of the CD4 lymphocyte depleting agent and a therapeutically effective amount of the checkpoint inhibitor thereby treating, preventing, reducing the severity of and/or slowing the progression of the condition in the subject.

Various embodiments of the present invention provide methods for treating, preventing, reducing the severity of and/or slowing the progression of a condition in a subject. The methods include providing a CD4 lymphocyte depleting agent, a dendritic cell (DC) vaccine and an mTOR inhibitor and administering an effective amount each of the CD4 lymphocyte depleting agent, dendritic cell vaccine and an mTOR inhibitor thereby treating, preventing, reducing the severity of and/or slowing the progression of the condition in the subject.

Various embodiments of the present invention provide a pharmaceutical composition comprising a CD4 lymphocyte depleting agent. Further embodiments provide pharmaceutical compositions comprising any one of an immune check point inhibitor, an adoptive immune therapeutic, an immune adjuvant, and an immune modulating agent.

Various embodiments of the present invention provide a kit for treating, preventing, reducing the severity of and/or slowing the progression of a condition in a subject. The kit includes a CD4 lymphocyte depleting agent and instructions for using the composition to treat, prevent, reduce the severity of and/or slow the progression of the condition in the subject.

Various embodiments of the present invention provide a kit for treating, preventing, reducing the severity of and/or slowing the progression of a condition in a subject. The kit includes a CD4 lymphocyte depleting agent and at least one of an immune check point inhibitor, an adoptive immune therapeutic, an immune adjuvant, and an immune modulating agent. The kit further comprises instructions for using the CD4 lymphocyte depleting agent and the at least one of the immune check point inhibitor, the adoptive immune therapeutic, the immune adjuvant, and the immune modulating agent to treat, prevent, reduce the severity of and/or slow the progression of the condition in the subject.

In various embodiments, the condition is cancer. In exemplary embodiments, the cancer may be any of kidney cancer, melanoma, prostate cancer, breast cancer, glioblastoma, lung cancer, colon cancer, or bladder cancer. In some embodiments, the condition is an infectious disease.

Various methods, compositions and kits of the present invention find utility in the treatment of cancer or infectious diseases. In exemplary embodiments, the methods, compositions and kits of the present invention find utility in the treatment of certain subsets of malignant neoplastic cell proliferative disorders or diseases, including but not limited to carcinomas and melanomas. In exemplary embodiments, carcinomas include renal cell carcinomas.

BRIEF DESCRIPTION OF THE DRAWINGS

Exemplary embodiments are illustrated in referenced figures. It is intended that the embodiments and figures disclosed herein are to be considered illustrative rather than restrictive.

DETAILED DESCRIPTION OF THE INVENTION

Figure 1:
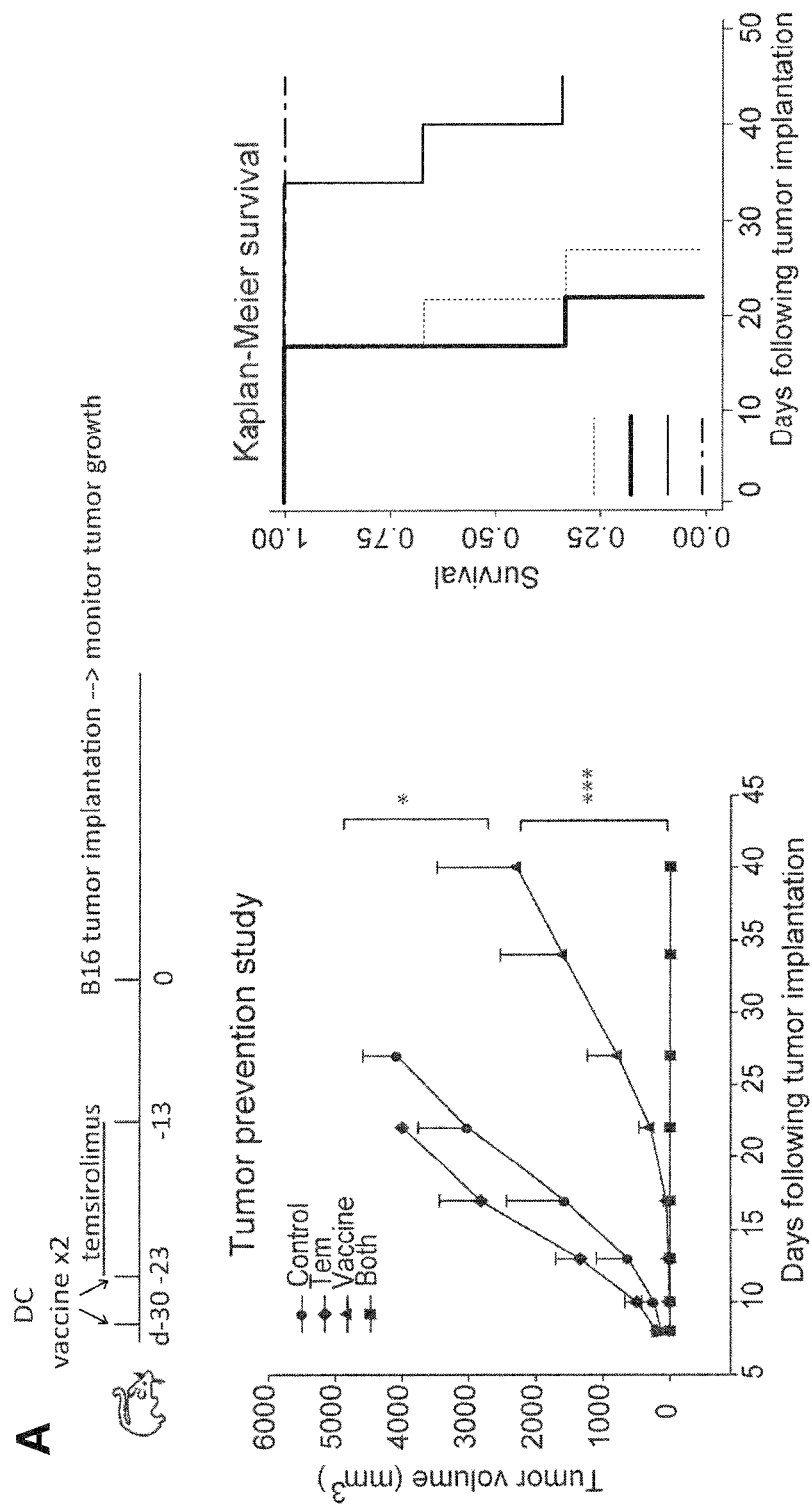
FIG. 1 depicts, in accordance with various embodiments of the invention, that there are both immune stimulating and inhibiting effects of mTOR inhibition; however the net effect is enhanced anti-tumor immunity. (a) Experimental scheme for a melanoma tumor prevention model: mice (n=5 per group) received tumor lysate-pulsed DC vaccine on days −30 and −23, and temsirolimus was injected intraperitoneally daily on days −23 to −13. B16 tumor cells were injected subcutaneously in the flank on day 0. B16 tumor growth (left) and survival (right) curves are shown. Results are representative of duplicate experiments. (b) Experimental scheme to characterize lymphocytes following treatment with DC vaccine and temsirolimus: Thy1.1 Pmel-1 lymphocytes were adoptively transfer into Thy1.2 B6 mice, which received tumor lysate-pulsed DC vaccine on day −6, and daily temsirolimus for 5 days. Splenocytes were harvested on day 0, and stained for CD8, Thy1.1, Tbet, Eomes and CD4/FoxP3 and analyzed by flow cytometry. Representative result (left) and summary data (right) are provided. Results are representative of duplicate experiments. (c) Lymphocytes were characterized with in vitro mixed cultures using pmel-1 lymphocytes and tumor lysate-pulsed, CpG activated DCs treated with temsirolimus for 48 hours. Lymphocytes were stained for CD8, Thy1.1, Tbet, Eomes and CD4/FoxP3 and analyzed by flow cytometry. Representative result (left) and summary data (right) are provided. Results are representative of duplicate experiments. $*p<0.05$, $p<0.01$, $*p<0.005$.
Figure 1:
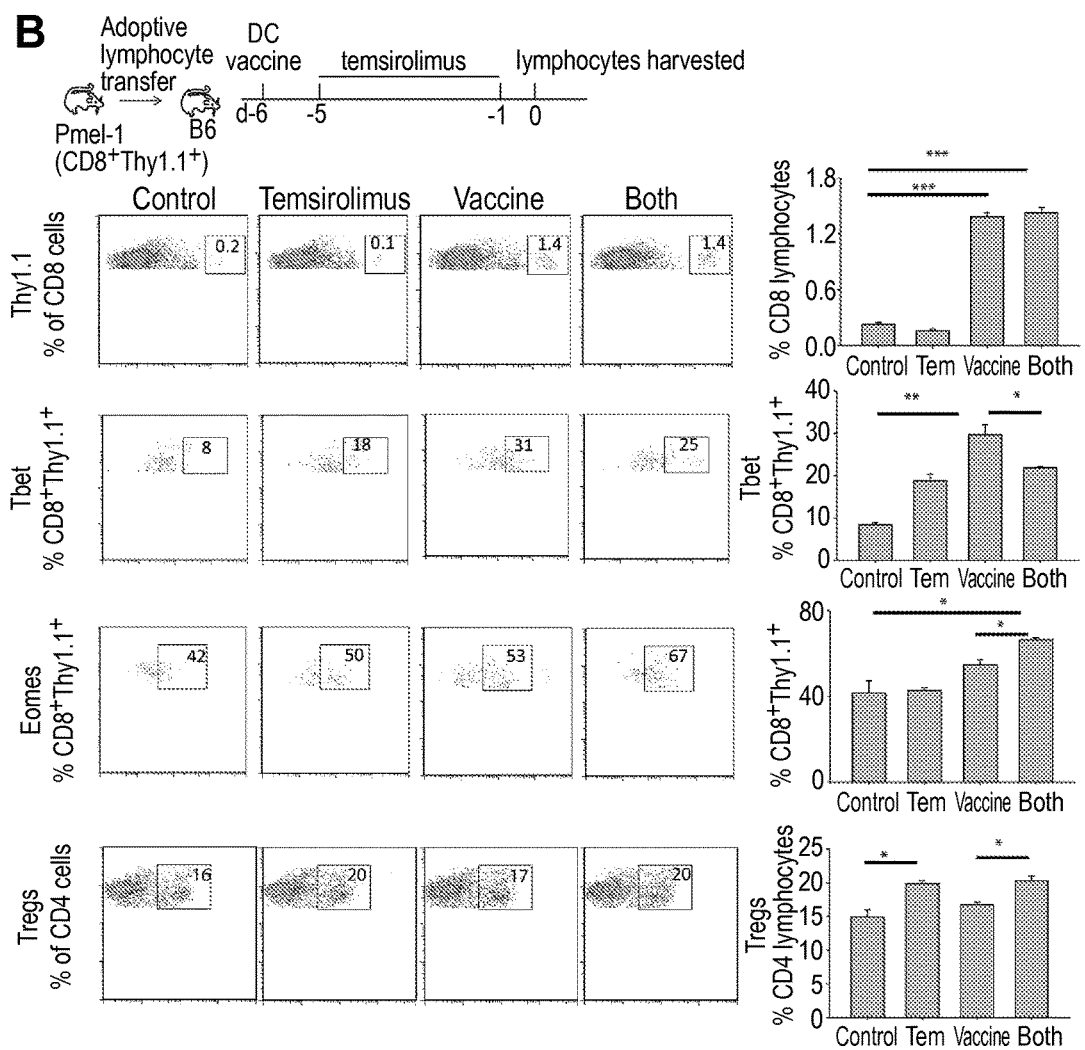
Figure 1:
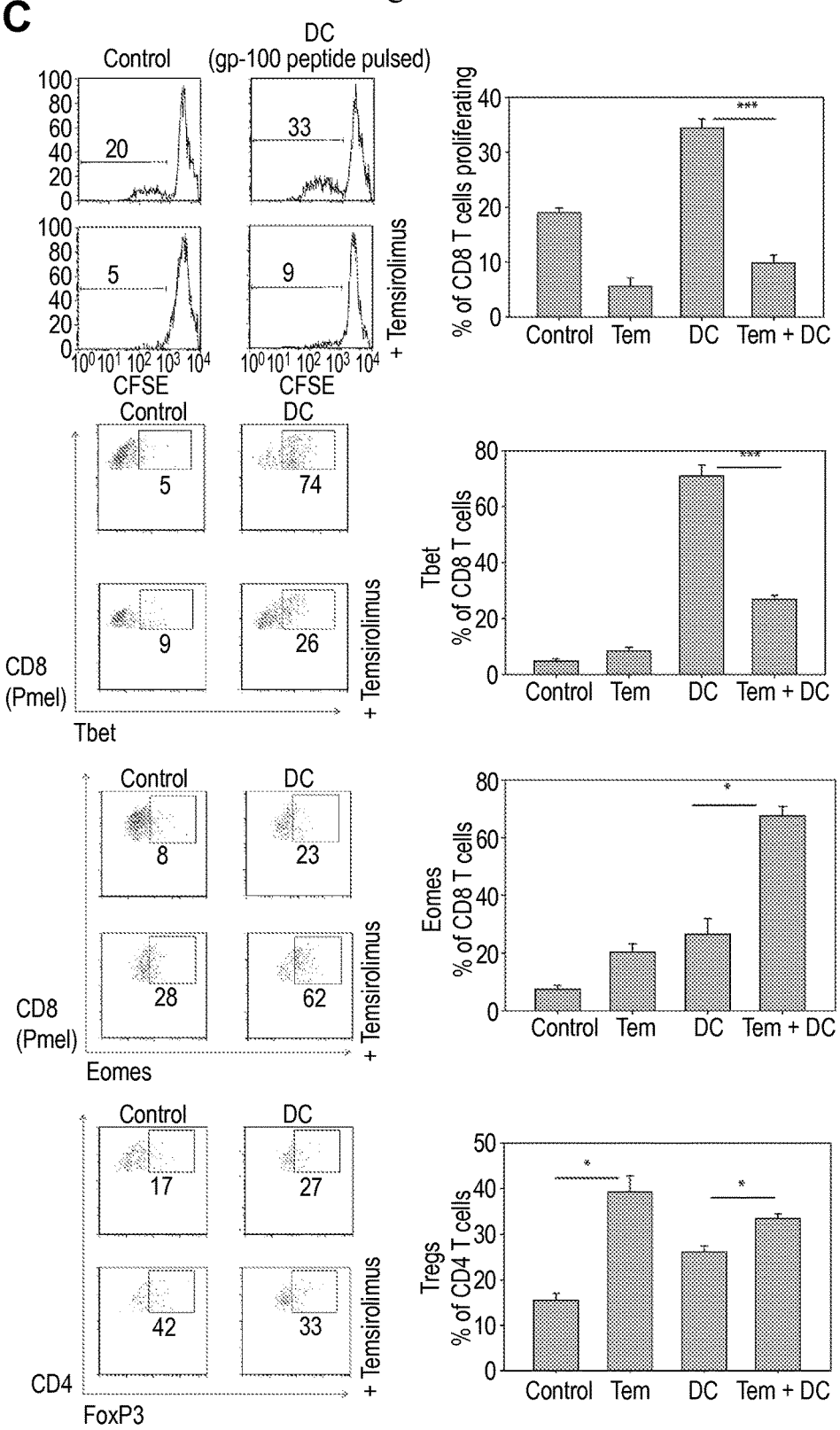

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* $22^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* $3^{rd}$ ed., revised ed., J. Wiley & Sons (New York, N.Y. 2006); Smith, *March's Advanced Organic Chemistry Reactions, Mechanisms and Structure* $7^{th}$ ed., J. Wiley & Sons (New York, N.Y. 2013); Singleton, *Dictionary of DNA and Genome Technology* $3^{rd}$ ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, N.Y. 2012), provide one skilled in the art with a general guide to many of the terms used in the present application. For references on how to prepare antibodies, see Greenfield, *Antibodies A Laboratory Manual* $2^{nd}$ ed., Cold Spring Harbor Press (Cold Spring Harbor N.Y., 2013); Köhler and Milstein, *Derivation of specific antibody-producing tissue culture and tumor lines by cell fusion*, Eur. J. Immunol. 1976 July, 6(7):511-9; Queen and Selick, *Humanized immunoglobulins*, U.S. Pat. No. 5,585,089 (1996 December); and Riechmann et al., *Reshaping human antibodies for therapy*, Nature 1988 Mar. 24, 332(6162):323-7.

For references on pediatrics, see Schwartz et al., *The 5-Minute Pediatric Consult* 4th ed., Lippincott Williams & Wilkins, (Jun. 16, 2005); Robertson et al., *The Harriet Lane Handbook: A Manual for Pediatric House Officers* $17^{th}$ ed., Mosby (Jun. 24, 2005); and Hay et al., *Current Diagnosis and Treatment in Pediatrics (Current Pediatrics Diagnosis & Treatment)* $18^{th}$ ed., McGraw-Hill Medical (Sep. 25, 2006).

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

As used herein, the terms "treat," "treatment," "treating," or "amelioration" when used in reference to a disease, disorder or medical condition, refer to both therapeutic treatment and prophylactic or preventative measures, wherein the object is to prevent, reverse, alleviate, ameliorate, inhibit, lessen, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a disease-state is reduced or halted. That is, "treatment" includes not just the improvement of symptoms or markers, but also a cessation or at least slowing of progress or worsening of symptoms that would be expected in the absence of treatment. Also, "treatment" may mean to pursue or obtain beneficial results, or lower the chances of the individual developing the condition even if the treatment is ultimately unsuccessful. Those in need of treatment include those already with the condition as well as those prone to have the condition or those in whom the condition is to be prevented.

"Beneficial results" or "desired results" may include, but are in no way limited to, lessening or alleviating the severity of the disease condition, preventing the disease condition from worsening, curing the disease condition, preventing the disease condition from developing, lowering the chances of a patient developing the disease condition, decreasing morbidity and mortality, and prolonging a patient's life or life expectancy. As non-limiting examples, "beneficial results" or "desired results" may be alleviation of one or more symptom(s), diminishment of extent of the deficit, stabilized (i.e., not worsening) state of cancer progression, delay or slowing of metastasis or invasiveness, and amelioration or palliation of symptoms associated with the cancer.

As used herein, the term "administering," refers to the placement an agent as disclosed herein into a subject by a method or route which results in at least partial localization of the agents at a desired site.

A "cancer" or "tumor" as used herein refers to an uncontrolled growth of cells which interferes with the normal functioning of the bodily organs and systems, and/or all neoplastic cell growth and proliferation, whether malignant or benign, and all pre-cancerous and cancerous cells and tissues. Included in this definition are benign and malignant cancers, as well as dormant tumors or micro-metastases. As used herein, the term "carcinoma" refers to a cancer arising from epithelial cells. As used herein, the term "invasive" refers to the ability to infiltrate and destroy surrounding tissue. Melanoma is an invasive form of skin tumor. Examples of cancer include, but are not limited to B-cell lymphomas (Hodgkin's lymphomas and/or non-Hodgkins lymphomas), brain tumor, breast cancer, colon cancer, lung cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, brain cancer, and prostate cancer, including but not limited to androgen-dependent prostate cancer and androgen-independent prostate cancer.

"Conditions" and "disease conditions," as used herein may include, cancers, tumors or infectious diseases. In exemplary embodiments, the conditions include but are in no way limited to any form of malignant neoplastic cell proliferative disorders or diseases. In exemplary embodiments, conditions include any one or more of kidney cancer, melanoma, prostate cancer, breast cancer, glioblastoma, lung cancer, colon cancer, or bladder cancer.

"Immune cell" as used herein refers to the cells of the mammalian immune system including but not limited to antigen presenting cells, B-cells, basophils, cytotoxic T-cells, dendritic cells, eosinophils, granulocytes, helper T-cells, leukocytes, lymphocytes, macrophages, mast cells, memory cells, monocytes, natural killer cells, neutrophils, phagocytes, plasma cells and T-cells.

"Immune response" as used herein refers to immunities including but not limited to innate immunity, humoral immunity, cellular immunity, immunity, inflammatory response, acquired (adaptive) immunity, autoimmunity and/or overactive immunity The term "sample" or "biological sample" as used herein denotes a sample taken or isolated from a biological organism, e.g., a tumor sample from a subject. Exemplary biological samples include, but are not limited to, a biofluid sample; serum; plasma; urine; saliva; a tumor sample; a tumor biopsy and/or tissue sample etc. The term also includes a mixture of the above-mentioned samples. The term "sample" also includes untreated or pretreated (or pre-processed) biological samples. In some embodiments, a sample can comprise one or more cells from the subject. In some embodiments, a sample can be a tumor cell sample, e.g. the sample can comprise cancerous cells, cells from a tumor, and/or a tumor biopsy.

The term "functional" when used in conjunction with "derivative" or "variant" or "fragment" refers to a polypeptide which possess a biological activity that is substantially similar to a biological activity of the entity or molecule of which it is a derivative or variant or fragment thereof.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. The terms, "patient", "individual" and "subject" are used interchangeably herein. In an embodiment, the subject is mammal. The mammal can be a human, non-human primate, mouse, rat, dog, cat, horse, or cow, but are not limited to these examples. In addition, the methods described herein can be used to treat domesticated animals and/or pets.

A subject can be one who has been previously diagnosed with or identified as suffering from or having a disease-state in need of monitoring (e.g., cancer or infectious disease) or one or more complications related to such a disease-state, and optionally, have already undergone treatment for the disease-state or the one or more complications related to the disease/condition. Alternatively, a subject can also be one who has not been previously diagnosed as having a disease-state or one or more complications related to the disease/condition. For example, a subject can be one who exhibits one or more risk factors for a disease-state or one or more complications related to a disease-state or a subject who does not exhibit risk factors. A "subject in need" of treatment for a particular disease-state can be a subject having that disease/condition, diagnosed as having that condition, or at risk of developing that disease.

The term "statistically significant" or "significantly" refers to statistical evidence that there is a difference. It is defined as the probability of making a decision to reject the null hypothesis when the null hypothesis is actually true. The decision is often made using the p-value.

As used herein, "CD4 lymphocytes" refer to lymphocytes that express CD4, i.e., lymphocytes that are CD4+. CD4 lymphocytes may be T cells that express CD4.

The terms "T-cell" and "T-lymphocyte" are interchangeable and used synonymously herein. Examples include but are not limited to naïve T cells, central memory T cells, effector memory T cells or combinations thereof.

"Therapeutic agents" as used herein refers to agents that are used to, for example, treat, inhibit, prevent, mitigate the effects of, reduce the severity of, reduce the likelihood of developing, slow the progression of and/or cure, a disease. Diseases targeted by the therapeutic agents include but are not limited to infectious diseases, carcinomas, sarcomas, lymphomas, leukemia, germ cell tumors, blastomas, antigens expressed on various immune cells, and antigens expressed on cells associated with various hematologic diseases, and/or inflammatory diseases.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

Provided herein are methods, compositions and kits, in which a CD4 lymphocyte depleting agent is used alone or in combination with various other therapies and agents to target the immune system to treat cancer and/or infectious diseases. Non-limiting examples of therapies and agents that can be used in combination with a CD4 lymphocyte depleting agent include but are not limited to immune check point inhibitors, adoptive immune therapies, immune adjuvants, and immune modulating agents.

Treatment Methods

In various embodiments, the present invention provides a method of treating, preventing, reducing the severity of and/or slowing the progression of a condition in a subject. The method includes providing a composition comprising a CD4 lymphocyte depleting agent and administering a therapeutically effective amount of the composition to the subject, thereby treating, preventing, reducing the severity of and/or slowing the progression of the condition in the subject. In some embodiment, the condition is cancer or an infectious disease. In some embodiments, the subject has been diagnosed with cancer. In some embodiments, the subject has been diagnosed with an infectious disease. In various embodiments, the subject has had the disease for an amount of time long enough to prime the immune system prior to administration of the composition comprising a CD4 lymphocyte depleting agent. In various embodiments, the amount of time for which the subject has had the condition is 1 day or more, 2 days or more, 3 days or more, 4 days or more, 5 days or more, 6 days or more, 7 days or more, 8 days or more, 9 days or more, 10 days or more, 15 days or more, 20 days or more, 1 month or more, 2 months or more, 3 months or more, 4 months or more, 5 months or more, 6 months or more, 1 year or more, or combinations thereof.

In various embodiments, the present invention provides methods for treating, preventing, reducing the severity of and/or slowing the progression of a condition in a subject. The methods include providing a CD4 lymphocyte depleting agent and at least one additional agent selected from the group consisting of an immune check point inhibitor, an adoptive immune therapeutic agent, an immune adjuvant, and an immune modulating agent; and administering a therapeutically effective amount of the CD4 lymphocyte depleting agent and a therapeutically effective amount of at least one of an immune check point inhibitor, an adoptive immune therapeutic agent, an immune adjuvant, and an immune modulating agent to the subject, thereby treating, preventing, reducing the severity of and/or slowing the progression of the condition in the subject. In some embodiment, the methods further comprise administering an mTOR inhibitor to the subject. In various embodiments, the CD4 lymphocyte depleting agent and the additional agent may be administered sequentially or simultaneously. In some embodiments, the condition is cancer. In some embodiments, the condition is an infectious disease.

In various embodiments, the present invention provides methods for treating, preventing, reducing the severity of and/or slowing the progression of a condition in a subject. The methods include providing a CD4 lymphocyte depleting agent and an adoptive immune therapeutic agent and administering a therapeutically effective amount of the CD4 lymphocyte depleting agent and a therapeutically effect amount of the adoptive immune therapeutic agent to the subject so as to treat, inhibit, prevent, reduce the severity and/or slow the progression of the condition in the subject. In an embodiment, the CD4 lymphocyte depleting agent is an anti-CD4 antibody or a fragment thereof or a variant thereof and the adoptive immune therapeutic agent is a dendritic cell vaccine. In various embodiments, the condition is cancer or an infectious disease. In some embodiments, anti-CD4 antibody and dendritic cell vaccine are administered simultaneously. In some embodiments, the anti-CD4 antibody and the dendritic cell vaccine are administered sequentially. In some embodiments, the methods may further comprise administering an effective amount of an mTOR inhibitor, sequentially or simultaneously with the CD4 lymphocyte depleting agent and the adoptive immune therapeutic agent.

In various embodiments, the present invention provides methods for treating, preventing, reducing the severity of and/or slowing the progression of a condition in a subject. The methods include providing a CD4 lymphocyte depleting agent and an immune checkpoint inhibitor and administering a therapeutically effective amount of the CD4 lymphocyte depleting agent and a therapeutically effective amount of the immune checkpoint inhibitor to the subject so as to treat, inhibit, prevent, reduce the severity and/or slow the progression of the condition in the subject. In an embodiment, the CD4 lymphocyte depleting agent is an anti-CD4 antibody or a fragment thereof or a variant thereof and the checkpoint inhibitor is an anti-PD-1 antibody or a fragment thereof or a variant thereof. In various embodiments, the condition is cancer or an infectious disease. In some embodiments, anti-CD4 antibody and anti-PD-1 antibody are administered simultaneously. In some embodiments, the anti-CD4 antibody and the anti-PD-1 antibody are administered sequentially. The methods may further comprise administering an mTOR inhibitor. In some embodiments, the methods may further comprise administering an effective amount of an mTOR inhibitor, sequentially or simultaneously with the CD4 lymphocyte depleting agent and the checkpoint inhibitor.

In various embodiments, the present invention provides methods for treating, preventing, reducing the severity of and/or slowing the progression of a condition in a subject. The methods include providing a CD4 lymphocyte depleting agent, an adoptive immune therapeutic agent and an mTOR inhibitor and administering a therapeutically effective amount of the CD4 lymphocyte depleting agent, a therapeutically effective amount of the adoptive immune therapeutic agent and a therapeutically effective amount of the mTOR inhibitor to the subject so as to treat, inhibit, prevent, reduce the severity and/or slow the progression of the condition in the subject. In an embodiment, the CD4 lymphocyte depleting agent is an anti-CD4 antibody or a fragment thereof or a variant thereof. In an embodiment, the adoptive immune therapeutic agent is a dendritic cell vaccine. In an embodiment, the mTOR inhibitor is temsirolimus. In various embodiments, the condition is cancer or an infectious disease. In some embodiments, anti-CD4 antibody, dendritic cell vaccine and the mTOR inhibitor (for example temsirolimus) are administered simultaneously. In some embodiments, anti-CD4 antibody, dendritic cell vaccine and the mTOR inhibitor (for example temsirolimus) are administered sequentially.

In various embodiments, the methods described herein may be used to prevent metastasis of cancer or prevent recurrence of cancer in a subject in need thereof.

In various embodiments of the invention, the CD4 lymphocyte depleting agent may be any one or more of small molecule, a peptide, an antibody or a fragment thereof, and a nucleic acid molecule. In an embodiment, the antibody specifically binds CD4 on CD4-expressing T cells such as regulatory T cells (Treg cells).

An antibody (for example, anti-CD4 antibody or anti-PD-1 antibody) may be any one or more of a monoclonal antibody or fragment thereof, a polyclonal antibody or a fragment thereof, a chimeric antibody, a humanized antibody, a human antibody or a fragment thereof, or a single chain antibody. These antibodies can be from any source, e.g., rat, mouse, guinea pig, dog, cat, rabbit, pig, cow, horse, goat, donkey or human. Fragments of antibodies may be any one or more of Fab, F(ab')2, Fv fragments or their fusion proteins.

In various embodiments, the CD4 lymphocyte depleting agent is a humanized anti-CD4 antibody or a fragment thereof. In various embodiments, the CD4 lymphocyte depleting agents are zanolimumab, keliximab, and OKT4.

In some embodiments of the invention, the CD4 lymphocyte depleting agent and the additional agent are administered concurrently. In other embodiments, the CD4 lymphocyte depleting agent and the additional agent are administered sequentially. For example, the CD4 lymphocyte depleting agent is administered before, during or after administering the additional agent. In further embodiments, the the CD4 lymphocyte depleting agent and the additional agent are administered with food or without food. In accordance with the invention, the CD4 lymphocyte depleting agent and/or the additional agent may be used in combination with other agents, including but not limited to cancer vaccines and chemotherapeutic agents. As described herein, the additional agent is any one or more of an immune check point inhibitor, an adoptive immune therapeutic agent, an immune adjuvant, and an immune modulating agent.

In various embodiments, the additional agent is an immune checkpoint inhibitor. Examples of immune checkpoint inhibitors include but are not limited to anti-PD-1 antibodies such as Lambrolizumab (MK-3475), Nivolumab (BMS-936558) and Pidilizumab (CT-011), anti-PD-L1 antibodies such as MPDL3280A(RG7446), MEDI4736 and BMS-936559, anti-PD-L2 antibodies, B7-DC-Fc fusion proteins such as AMP-224, anti-CTLA-4 antibodies such as tremelimumab (CP-675,206) and ipilimumab (MDX-010), antibodies against the B7/CD28 receptor superfamily, anti-Indoleamine (2,3)-dioxygenase (IDO) antibodies, anti-IDO1 antibodies, anti-IDO2 antibodies, tryptophan, tryptophan mimetic, 1-methyl tryptophan (1-MT)), Indoximod (D-1-methyl tryptophan (D-1-MT)), L-1-methyl tryptophan (L-1-MT), TX-2274, hydroxyamidine inhibitors such as INCB024360, anti-TIM-3 antibodies, anti-LAG-3 antibodies such as BMS-986016, recombinant soluble LAG-3Ig fusion proteins that agonize MHC class II-driven dendritic cell activation such as IMP321, anti-KIR2DL1/2/3 or anti-KIR) antibodies such lirilumab(IPH2102), urelumab (BMS-663513), anti-phosphatidylserine (anti-PS) antibodies such as Bavituximab, anti-idiotype murine monoclonal antibodies against the human monoclonal antibody for N-glycolil-GM3 ganglioside such as Racotumomab (formerly known as 1E10), anti-OX40R antibodies such as IgG CD134 mAb, anti-B7-H3 antibodies such as MGA271, and small interfering (si) RNA-based cancer vaccines designed to treat cancer by silencing immune checkpoint genes. Additional information can be found in Creelan BC (Update on immune checkpoint inhibitors in lung cancer, Cancer Control. 2014 January; 21(1):80-9) and Jane de Lartigue (Another Immune Checkpoint Emerges as Anticancer Target, Published online by onclive.com, Tuesday, Sep. 24, 2013), which are incorporated herein by reference in their entirety as though fully set forth. In some embodiments, the immune checkpoint inhibitor is selected from the group consisting of an antibody against PD-1, an antibody against PD-L1, an antibody against PD-L2, an antibody against CTLA-4, an antibody against KIR, an antibody against IDO1, an antibody against IDO2, an antibody against TIM-3, an antibody against LAG-3, an antibody against OX40R, and an antibody against PS, or a combination thereof.

In various embodiments, the additional agent is an adoptive immune therapeutic. In some embodiments, the adoptive immune therapeutic is selected from the group consisting of a dendritic cell vaccine, a peptide vaccine, a chimeric T cell antigen-based therapy, T cell-based therapy, an immune cytokine, a heat shock protein-based vaccine, a tumor lysate-based vaccine, a viral vector carrying a tumor antigen, a viral vaccine, a bacterial vaccine, and a fungal vaccine, or a combination thereof. Additional information can be found in Radvanyi et al. Clin Cancer Res. 2012 Dec. 15; 18(24):6758-70; Epub 2012 Oct. 2, which is incorporated herein by reference in its entirety as though fully set forth.

In various embodiments, the additional agent is an immune adjuvant. Examples of adjuvants include but are not limited to cationic liposome-DNA complex JVRS-100, aluminum hydroxide vaccine adjuvant, aluminum phosphate vaccine adjuvant, aluminum potassium sulfate adjuvant, Alhydrogel, ISCOM(s)™, Freund's Complete Adjuvant, Freund's Incomplete Adjuvant, CpG DNA Vaccine Adjuvant, Cholera toxin, Cholera toxin B subunit, Liposomes, Saponin Vaccine Adjuvant, DDA Adjuvant, Squalene-based Adjuvants, Etx B subunit Adjuvant, IL-12 Vaccine Adjuvant, LTK63 Vaccine Mutant Adjuvant, TiterMax Gold Adjuvant, Ribi Vaccine Adjuvant, Montanide ISA 720 Adjuvant, Corynebacterium-derived P40 Vaccine Adjuvant, MPL™ Adjuvant, AS04, AS02, Lipopolysaccharide Vaccine Adjuvant, Muramyl Dipeptide Adjuvant, CRL1005, Killed Corynebacterium parvum Vaccine Adjuvant, Montanide ISA 51, Bordetella pertussis component Vaccine Adjuvant, Cationic Liposomal Vaccine Adjuvant, Adamantylamide Dipeptide Vaccine Adjuvant, Arlacel A, VSA-3 Adjuvant, Aluminum vaccine adjuvant, Polygen Vaccine Adjuvant, Adjumer™, Algal Glucan, Bay R1005, Theramide®, Stearyl Tyrosine, Specol, Algammulin, Avridine®, Calcium Phosphate Gel, CTAT-DD gene fusion protein, DOC/Alum Complex, Gamma Inulin, Gerbu Adjuvant, GM-CSF, GMDP, Recombinant hIFN-gamma/Interferon-g, Interleukin-1β, Interleukin-2, Interleukin-7, Sclavo peptide, Rehydragel LV, Rehydragel HPA, Loxoribine, MF59, MTP-PE Liposomes, Murametide, Murapalmitine, D-Murapalmitine, NAGO, Non-Ionic Surfactant Vesicles, PMMA, Protein Cochleates, QS-21, SPT (Antigen Formulation), nanoemulsion vaccine adjuvant, AS03, Quil-A vaccine adjuvant, RC529 vaccine adjuvant, LTR192G Vaccine Adjuvant, E. coli heat-labile toxin, LT, amorphous aluminum hydroxyphosphate sulfate adjuvant, Calcium phosphate vaccine adjuvant, Montanide Incomplete Seppic Adjuvant, Imiquimod, Resiquimod, AF03, Flagellin, Poly(I:C), ISCOMATRIX®, Abisco-100 vaccine adjuvant, Albumin-heparin microparticles vaccine adjuvant, AS-2 vaccine adjuvant, B7-2 vaccine adjuvant, DHEA vaccine adjuvant, Immunoliposomes Containing Antibodies to Costimulatory Molecules, SAF-1, Sendai Proteoliposomes, Sendai-containing Lipid Matrices, Threonyl muramyl dipeptide (TMDP), Ty Particles vaccine adjuvant, Bupivacaine vaccine adjuvant, DL-PGL (Polyester poly (DL-lactide-co-glycolide)) vaccine adjuvant, IL-15 vaccine adjuvant, LTK72 vaccine adjuvant, MPL-SE vaccine adjuvant, non-toxic mutant E112K of Cholera Toxin mCT-E112K, Matrix-S, and water soluble triterpene glucoside compounds. Additional information can be found in Sayers et al., (VAXJO: A WEB-BASED VACCINE ADJUVANT DATABASE AND ITS APPLICATION FOR ANALYSIS OF VACCINE ADJUVANTS AND THEIR USES IN VACCINE DEVELOPMENT, 2012; 2012:831486; Epub 2012 Mar. 13), which is incorporated herein by reference in its entirety as though fully set forth. In some embodiments, the immune adjuvant is selected from the group consisting of an aluminum salt, a virosome and an oil-based adjuvant, or a combination thereof.

In various embodiments, the additional agent is an immune modulating agent. In some embodiments, the immune modulating agent is selected from the group consisting of an mTOR inhibitor, a STAT inhibitor, a TGFβ receptor inhibitor, and a tyrosine kinase inhibitor, or a combination thereof.

In various embodiments, the methods may further include administering an mTOR inhibitor to the subject. In accordance with the invention, the mTOR inhibitor may be any one or more of a small molecule, a peptide, an antibody or a fragment thereof, a nucleic acid molecule and/or a macrolide compound. In an embodiment, the antibody specifically binds mTOR so as to inhibit mTOR. The antibody may be any one or more of a monoclonal antibody or fragment thereof, a polyclonal antibody or a fragment thereof, a chimeric antibody, a humanized antibody, a human antibody or a fragment thereof, or a single chain antibody. These antibodies can be from any source, e.g., rat, mouse, guinea pig, dog, cat, rabbit, pig, cow, horse, goat, donkey or human. Fragments of antibodies may be any one or more of Fab, F(ab')2, Fv fragments or their fusion proteins.

In an embodiment of the invention, the mTOR inhibitor is a macrolide compound. Examples of macrolide compounds that may be used with the claimed invention include but are not limited to temsirolimus (CCI-779) or a pharmaceutical equivalent, analog, derivative or a salt thereof, evirolimus (RAD-001) or a pharmaceutical equivalent, analog, derivative or a salt thereof, and/or sirolimus (rapamycin) or a pharmaceutical equivalent, analog, derivative or a salt thereof.

In various embodiments, the additional agent is a STAT inhibitor. Examples of STAT inhibitors include but are not limited to SOCS (supressors of cytokine signaling), PIAS (protein inhibitors of activated stats) including PIAS1, PIAS2, PIAS3, PIAS4, PIASxa, PIASxb, and PIASy, Nifuroxazide (5-Nitro-2-furaldehyde-p-hydroxybenzoylhydrazone), N-[2-(1, 3, 4-oxadiazolyl)]-4-Quinolinecarboxamide, non-peptidic small molecule inhibitors, Stattic, STA-21, LLL-3, LLL12, XZH-5, S31-201, SF-1066, SF-1087, 17o, Cryptotanshinon, FLL32, C188-9, LY5, BP-1108, BP-1075, Galiellalactone, JQ1, STX-0119, FLLL11, FLLL12, FLLL32, FLLL62, hormone-derived nicotinyl hydrazine, IS3 295, oligonucleotides targeting STAT pathway, antisense oligonucleotide (ASO) targeting STAT pathway, AZD9150 (ISIS-STAT3Rx or ISIS 481464, a synthetic ASO against STAT3, STAT3 decoy oligonucleotide (ODN), STAT3-siRNA, STAT3-G-Quartet, STAT5-ODN, STAT5-siRNA, OPB-31121, peptides and peptidomimetics inhibitors, XpYL, Ac-pYLPQTV-NH3, ISS610, S31-M2001, and CJ-1383. Additional information can be found in Furqan et al. (STAT inhibitors for cancer therapy, J Hematol Oncol. 2013 Dec. 5; 6:90), which is incorporated herein by reference in its entirety as though fully set forth.

In various embodiments, the additional agent is a JAK inhibitor. Examples of JAK inhibitors include but are not limited to Tyrphostin AG490, CP-690550, ruxolitinib (INCB018424), TG101348 (SAR 30253), lestaurtinib (CEP701), CYT387, pacritinib (SB1518), AZD1480, XL019, and LY2784544. Additional information can be found in Mascarenhas et al. (Biology and clinical management of myeloproliferative neoplasms and development of the JAK inhibitor ruxolitinib, Curr Med Chem. 2012; 19(26):4399-413), which is incorporated herein by reference in its entirety as though fully set forth.

In various embodiments, the additional agent is a TGFβ receptor inhibitor. Examples of TGFβ receptor inhibitors include but are not limited to dominant negative TGF-β Type II receptors (TβRII), ligand traps, the soluble TβRII ectodomain, the soluble betaglycan ectodomain, recombinant Fc-fusion proteins containing the soluble ectodomain of either TβRII (TβRII-Fc) or the type III receptor/betaglycan, soluble human α2-macroglobulin plasma protein, fully humanized pan-TGF-β monoclonal neutralizing antibodies including Lerdelimumab (CAT-152), Metelimumab (CAT-192) and GC-1008 (Fresolimumab), and 1D11; antisense oligonucleotides (ASO) designed to hybridize to their complementary RNA sequence and accelerate mRNA degradation, AP12009 (Trabedersen) and AP-11014; receptor kinase inhibitors, SB505124, SB-431542, LY550410, LY580276, LY215729, LY364937, LY2109761, Ki26894, SD-093 and SD-208; peptide aptamers, the Trx-SARA aptamer; vectors coding for small hairpin RNA which silence TGF-β receptor Type II gene expression by RNA interference, and shRNA with lentiviral or adeno-associated vectors. Additional information can be found in Connolly et al. (Complexities of TGF-β targeted cancer therapy, Int J Biol Sci. 2012; 8(7):964-78; Epub 2012 Jul. 12) and Kaminska et al. (TGF beta signalling and its role in tumour pathogenesis; Acta Biochim Pol. 2005; 52(2):329-37. Epub 2005 Jun. 25), which are incorporated herein by reference in their entirety as though fully set forth.

In various embodiments, the additional agent is a tyrosine kinase inhibitor. Examples of tyrosine kinase inhibitors include but are not limited to sunitinib, erlotinib, vandetanib, cediranib, brivanib, foretinib, and dovitinib. Additional information can be found in Huynh H. (Molecularly targeted therapy in hepatocellular carcinoma, Biochem Pharmacol. 2010 Sep. 1; 80(5):550-60. Epub 2010 Apr. 4), which is incorporated herein by reference in its entirety as though fully set forth.

In some embodiments, the methods described herein further comprise administering a chemotherapeutic agent to the subject being administered a composition comprising CD4 lymphocyte depleting agent or a composition comprising a CD4 lymphocyte depleting agent and an additional agent selected from the group consisting of an immune check point inhibitor, an adoptive immune therapeutic, an immune adjuvant, and an immune modulating agent. Non-limiting examples of chemotherapeutic agents can include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE; vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above. In addition, the methods of treatment can further include the use of radiation therapy.

Examples of cancer include but are not limited to, carcinoma, blastoma, and sarcoma. More particular examples of such cancers include, but are not limited to, basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas.

In accordance with the invention, the condition may be a malignant neoplastic cell proliferative disorder or disease. Still in accordance with the invention, the condition may be renal cell carcinoma or melanoma. Diseases targeted by the therapeutic agents include carcinomas, sarcomas, germ cell tumors and/or blastomas.

In various embodiments, infectious diseases are caused by infectious bacteria. Examples of infectious bacteria include: *Helicobacterpyloris, Borelia burgdorferi, Legionella pneumophilia, Mycobacteria* sps (such as *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus anthracis, corynebacterium diphtheriae, corynebacterium* sp., *Erysipelothrix rhusiopathiae, Clostridium perfringens, Clostridium tetani, Enterobacter aerogenes, Klebsiella pneumoniae, Pasteurella multocida, Bacteroides* sp., *Fusobacterium nucleatum, Streptobacillus moniliformis, Treponema pallidium, Treponema pertenue, Leptospira,* and *Actinomyces israelli*. The compositions and methods described herein are contemplated for use in treating infections with these bacterial agents. Other infectious organisms (such as protists) include: *Plasmodium falciparum* and *Toxoplasma gondii*. The compositions and methods described herein are contemplated for use in treating infections with these agents.

In various embodiments, viral antigens may be any antigens present in infectious viruses and that induce an immune response in a subject. Examples of infectious viruses include: Retroviridae (for example, HIV); Picornaviridae (for example, polio viruses, hepatitis A virus; enteroviruses, human coxsackie viruses, rhinoviruses, echoviruses); Calciviridae (such as strains that cause gastroenteritis); Togaviridae (for example, equine encephalitis viruses, rubella viruses); Flaviridae (for example, dengue viruses, encephalitis viruses, yellow fever viruses); Coronaviridae (for example, coronaviruses); Rhabdoviridae (for example, vesicular stomatitis viruses, rabies viruses); Filoviridae (for example, ebola viruses); Paramyxoviridae (for example, parainfluenza viruses, mumps virus, measles virus, respiratory syncytial virus); Orthomyxoviridae (for example, influenza viruses); Bungaviridae (for example, Hantaan viruses, bunga viruses, phleboviruses and Nairo viruses); Arena viridae (hemorrhagic fever viruses); Reoviridae (e.g., reoviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and HSV-2, varicella zoster virus, cytomegalovirus (CMV), herpes viruses); Poxviridae (variola viruses, vaccinia viruses, pox viruses); and Iridoviridae (such as African swine fever virus); and unclassified viruses (for example, the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses). The compositions and methods described herein are contemplated for use in treating infections with these viral agents.

Examples of fungal infections that may be treated with the compositions and methods described herein include but are not limited to: aspergillosis; thrush (caused by *Candida albicans*); cryptococcosis (caused by *Cryptococcus*); and histoplasmosis. Thus, examples of infectious fungi include, but are not limited to, *Cryptococcus neoformans, Histoplasma capsulatum, Coccidioides immitis, Blastomyces dermatitidis, Chlamydia trachomatis, Candida albicans*. The compositions and methods described herein are contemplated for use in treating infections with these fungal agents.

In various embodiments, the subject is a human. In various embodiments, the subject is a a mammalian including but not limited to human, monkey, ape, dog, cat, cow, horse, goat, pig, rabbit, mouse and rat.

In various embodiments, the composition is administered intravenously, intramuscularly, subcutaneously, intraperitoneally, orally or via inhalation. In accordance with the invention, various routes may be utilized to administer the composition of the claimed methods, including but not limited to aerosol, nasal, oral, transmucosal, transdermal, parenteral, implantable pump, continuous infusion, topical application, capsules and/or injections.

In various embodiments, the CD4 lymphocyte depleting agent is administered at 100-200 mg/day, 200-300 mg/day, 300-400 mg/day, 400-500 mg/day, 500-600 mg/day, 600-700 mg/day, 700-800 mg/day, 800-900 mg/day, 900-1000 mg/day, 1000-1100 mg/day, 1100-1200 mg/day, 1200-1300 mg/day, 1300-1400 mg/day, 1400-1500 mg/day, 1500-1600 mg/day, 1600-1700 mg/day, 1700-1800 mg/day, 1800-1900 mg/day or 1900-2000 mg/day. In various embodiments, the additional agent is administered at 0.1-0.5 mg/day, 0.5-1.0 mg/day, 1.0-1.5 mg/day, 1.5-2.0 mg/day, 2.0-2.5 mg/day, 2.5-5 mg/day, 5-10 mg/day, 10-15 mg/day, 15-20 mg/day, 20-25 mg/day, 25-30 mg/day, 30-35 mg/day, 35-40 mg/day, 40-45 mg/day, 45-50 mg/day, 50-55 mg/day, 55-60 mg/day, 60-65 mg/day, 65-70 mg/day, 70-75 mg/day, 75-80 mg/day, 80-85 mg/day, 85-90 mg/day, 90-95 mg/day or 95-100 mg/day.

Pharmaceutical Compositions

In various embodiments, the present invention provides a composition comprising a CD4 lymphocyte depleting agent. In various embodiments, the present invention provides compositions comprising at least one of an immune check point inhibitor, an adoptive immune therapeutic, an immune adjuvant, and an immune modulating agent. Examples of immune check point inhibitor, an adoptive immune therapeutic, an immune adjuvant, and an immune modulating agent are described herein. In various embodiments, a composition comprising a CD4 lymphocyte depleting agent and a composition comprising an additional agent are two separate compositions.

In accordance with the invention, the CD4 lymphocyte depleting agents and/or the additional agents useful in the treatment of disease in mammals will often be prepared substantially free of naturally-occurring immunoglobulins or other biological molecules. Preferred CD4 lymphocyte depleting agents and/or the additional agents will also exhibit minimal toxicity when administered to a mammal.

The pharmaceutical compositions according to the invention can contain any pharmaceutically acceptable excipient. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous. Examples of excipients include but are not limited to starches, sugars, microcrystalline cellulose, diluents, granulating agents, lubricants, binders, disintegrating agents, wetting agents, emulsifiers, coloring agents, release agents, coating agents, sweetening agents, flavoring agents, perfuming agents, preservatives, antioxidants, plasticizers, gelling agents, thickeners, hardeners, setting agents, suspending agents, surfactants, humectants, carriers, stabilizers, and combinations thereof.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal, parenteral, enteral, topical or local. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the parenteral route, the compositions may be in the form of solutions or suspensions for infusion or for injection. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Typically, the compositions are administered by injection. Methods for these administrations are known to one skilled in the art.

The pharmaceutical compositions according to the invention can contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 20th edition, Williams & Wilkins Pa., USA) (2000).

Before administration to patients, formulants may be added to the composition. A liquid formulation may be preferred. For example, these formulants may include oils, polymers, vitamins, carbohydrates, amino acids, salts, buffers, albumin, surfactants, bulking agents or combinations thereof.

Carbohydrate formulants include sugar or sugar alcohols such as monosaccharides, disaccharides, or polysaccharides, or water soluble glucans. The saccharides or glucans can include fructose, dextrose, lactose, glucose, mannose, sorbose, xylose, maltose, sucrose, dextran, pullulan, dextrin, alpha and beta cyclodextrin, soluble starch, hydroxyethyl starch and carboxymethylcellulose, or mixtures thereof "Sugar alcohol" is defined as a C4 to C8 hydrocarbon having an —OH group and includes galactitol, inositol, mannitol, xylitol, sorbitol, glycerol, and arabitol. These sugars or sugar alcohols mentioned above may be used individually or in combination. There is no fixed limit to amount used as long as the sugar or sugar alcohol is soluble in the aqueous preparation. In one embodiment, the sugar or sugar alcohol concentration is between 1.0 w/v % and 7.0 w/v %, more preferable between 2.0 and 6.0 w/v %.

Amino acids formulants include levorotary (L) forms of carnitine, arginine, and betaine; however, other amino acids may be added.

In some embodiments, polymers as formulants include polyvinylpyrrolidone (PVP) with an average molecular weight between 2,000 and 3,000, or polyethylene glycol (PEG) with an average molecular weight between 3,000 and 5,000.

It is also preferred to use a buffer in the composition to minimize pH changes in the solution before lyophilization or after reconstitution. Most any physiological buffer may be used including but not limited to citrate, phosphate, succinate, and glutamate buffers or mixtures thereof. In some embodiments, the concentration is from 0.01 to 0.3 molar. Surfactants that can be added to the formulation are shown in EP Nos. 270,799 and 268,110.

Another drug delivery system for increasing circulatory half-life is the liposome. Methods of preparing liposome delivery systems are discussed in Gabizon et al., Cancer Research (1982) 42:4734; Cafiso, Biochem Biophys Acta (1981) 649:129; and Szoka, Ann Rev Biophys Eng (1980) 9:467. Other drug delivery systems are known in the art and are described in, e.g., Poznansky et al., DRUG DELIVERY SYSTEMS (R. L. Juliano, ed., Oxford, N.Y. 1980), pp. 253-315; M. L. Poznansky, Pharm Revs (1984) 36:277.

After the liquid pharmaceutical composition is prepared, it may be lyophilized to prevent degradation and to preserve sterility. Methods for lyophilizing liquid compositions are known to those of ordinary skill in the art. Just prior to use, the composition may be reconstituted with a sterile diluent (Ringer's solution, distilled water, or sterile saline, for example) which may include additional ingredients. Upon reconstitution, the composition is administered to subjects using those methods that are known to those skilled in the art.

The compositions of the invention may be sterilized by conventional, well-known sterilization techniques. The resulting solutions may be packaged for use or filtered under aseptic conditions and lyophilized, the lyophilized preparation being combined with a sterile solution prior to administration. The compositions may contain pharmaceutically-acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, and stabilizers (e.g., 1-20% maltose, etc.).

Kits of the Invention

In various embodiments, the present invention provides a kit for treating, preventing, reducing the severity of and/or slowing the progression of a condition in a subject. The kit comprises a composition comprising a CD4 lymphocyte depleting agent and instructions for using the composition to treat, prevent, reduce the severity of and/or slow the progression of the condition in the subject.

In various embodiments, the present invention provides a kit for treating, preventing, reducing the severity of and/or slowing the progression of a condition in a subject. The kit comprises a composition comprising a CD4 lymphocyte depleting agent and a composition comprising at least one additional agent selected from the group consisting of an immune check point inhibitor, an adoptive immune therapeutic, an immune adjuvant, and an immune modulating agent; and instructions for using the composition to treat, prevent, reduce the severity of and/or slow the progression of the condition in the subject.

The kit is an assemblage of materials or components, including at least one of the inventive compositions. Thus, in some embodiments the kit contains a composition including a drug delivery molecule complexed with a therapeutic agent, as described above.

The exact nature of the components configured in the inventive kit depends on its intended purpose. In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to affect a desired outcome. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. As used herein, the term "package" refers to a suitable solid matrix or material such as glass, plastic, paper, foil, and the like, capable of holding the individual kit components. Thus, for example, a package can be a glass vial used to contain suitable quantities of a composition containing a CD lymphocyte depleting agent or a composition containing a CD lymphocyte depleting agent and at least one additional agent selected from the group consisting of an immune check point inhibitor, an adoptive immune therapeutic, an immune adjuvant, and an immune modulating agent. The packaging material generally has an external label which indicates the contents and/or purpose of the kit and/or its components.

Dosages of the Invention

In some embodiments, the effective amounts of the CD4 lymphocyte depleting agent in the claimed methods, compositions and/or kits may be in the range of about 100-200 mg/day, 200-300 mg/day, 300-400 mg/day, 400-500 mg/day, 500-600 mg/day, 600-700 mg/day, 700-800 mg/day, 800-900 mg/day, 900-1000 mg/day, 1000-1100 mg/day, 1100-1200 mg/day, 1200-1300 mg/day, 1300-1400 mg/day, 1400-1500 mg/day, 1500-1600 mg/day, 1600-1700 mg/day, 1700-1800 mg/day, 1800-1900 mg/day or 1900-2000 mg/day. In one embodiment of the invention, the CD4 lymphocyte depleting agent is a humanized anti-CD4 antibody (for example zanolimumab).

In other embodiments, the effective amounts of the CD4 lymphocyte depleting agent in the claimed methods, compositions and/or kits may be in the range of about 100-200 mg/week, 200-300 mg/week, 300-400 mg/week, 400-500 mg/week, 500-600 mg/week, 600-700 mg/week, 700-800 mg/week, 800-900 mg/week, 900-1000 mg/week, 1000-1100 mg/week, 1100-1200 mg/week, 1200-1300 mg/week, 1300-1400 mg/week, 1400-1500 mg/week, 1500-1600 mg/week, 1600-1700 mg/week, 1700-1800 mg/week, 1800-1900 mg/week or 1900-2000 mg/week. In one embodiment of the invention, the CD4 lymphocyte depleting agent is a humanized anti-CD4 antibody (for example zanolimumab). Zanolimumab may be administered at a dose of 980 mg per week.

In some embodiments, the effective amounts of the additional agent in the claimed methods, compositions and/or kits may be in the range of about 0.1-0.5 mg/day, 0.5-1.0 mg/day, 1.0-1.5 mg/day, 1.5-2 mg/day, 2.0-2.5 mg/day, 2.5-5 mg/day, 5-10 mg/day, 10-15 mg/day, 15-20 mg/day, 20-25 mg/day, 25-30 mg/day, 30-35 mg/day, 35-40 mg/day, 40-45 mg/day, 45-50 mg/day, 50-55 mg/day, 55-60 mg/day, 60-65 mg/day, 65-70 mg/day, 70-75 mg/day, 75-80 mg/day, 80-85 mg/day, 85-90 mg/day, 90-95 mg/day, 95-100 mg/day, 0.75-10 mg/day or 2-10 mg/day. In various embodiments, the additional agents are any of immune check point inhibitor, an adoptive immune therapeutic, an immune adjuvant or an immune modulating agent.

In some embodiments, the effective amounts of the additional agent in the claimed methods, compositions and/or kits may be in the range of about 1-5 mg/week, 5-10 mg/week, 10-15 mg/week, 15-20 mg/week, 20-25 mg/week, 25-30 mg/week, 30-35 mg/week, 35-40 mg/week, 40-45 mg/week, 45-50 mg/week, 50-55 mg/week, 55-60 mg/week, 60-65 mg/week, 65-70 mg/week, 70-75 mg/day, 75-80 mg/mg, 80-85 mg/mg, 85-90 mg/week, 90-95 mg/week or 95-100 mg/week. In various embodiments, the additional agents are any of immune check point inhibitor, an adoptive immune therapeutic, an immune adjuvant or an immune modulating agent.

In some embodiments, the at least one additional agent comprises temsirolimus administered at a dose of 25 mg over 30-60 minutes per week, evirolimus administered at a dose of 0.75-10 mg per day and/or rapamycin administered at a dose of 2-10 mg per day.

In an embodiment of the claimed methods of the invention, the CD4 lymphocyte depleting agent and the additional agent may be administered simultaneously at the aforementioned dosages using the appropriate modes of administration, for instance, the modes of administration recommended by the manufacturer for each of the CD4 lymphocyte depleting agent and the additional agent.

Alternately, the CD4 lymphocyte depleting agent and the additional agent may be administered sequentially at the aforementioned dosages. For example, the additional agent may be administered, for example, daily at the aforementioned dosages and the CD4 lymphocyte depleting agent (for example a humanized anti-CD4 antibody) may be administered for example, daily, weekly, biweekly, every fortnight and/or monthly at the aforementioned dosages. Alternately, the additional agent may be administered, for example, daily, weekly, biweekly, every fortnight and/or monthly, at the aforementioned dosages and the CD4 lymphocyte depleting agent (for example a humanized anti-CD4 antibody) may be administered, for example, daily at the aforementioned dosages. Further, each of the additional agent and the CD4 lymphocyte depleting agent (for example a humanized anti-CD4 antibody) may be administered daily, weekly, biweekly, every fortnight and/or monthly, wherein the additional agent is administered at the aforementioned dosages on a day different than the day on which the CD4 lymphocyte depleting agent is administered at the aforementioned dosages.

The cancer vaccine dose would depend on the vaccine being used. The effective dose of the cancer vaccine may be determined by one skilled in the art (such as the physician) or it may be administered per the manufacturers' recommendation. In one embodiment, the first dose of the cancer vaccine is administered on day 0 and the second dose is administered on day 7. The additional agent may be administered on days 2-32, at the aforementioned dosages. Further, 2-3 weekly doses of anti-CD4 depleting agent may be administered starting on day 10, at the aforementioned dosages. For example, if a heat shock protein-based vaccine is used, a heat shock protein (for example, hsp110 or grp170) may be complexed with a tumor antigen (such as gp100) and subsequently administered. In an embodiment, for a melanoma vaccine, a complex of hsp110 and gp100 at 2.5 mg/kg, may be administered intradermally.

Typical dosages of an effective amount of the CD4 lymphocyte depleting agent or the additional agent can be in the ranges recommended by the manufacturer where known therapeutic compounds are used, and also as indicated to the skilled artisan by the in vitro responses in cells or in vivo responses in animal models.

For example, the FDA approved dosage for Temsirolimus is 25 mg administered intravenously over 30-60 min every week, for Evirolimus is 0.75 mg-10 mg per day administered orally, for Rapamycin is about 2-10 mg per day administered orally and for Zanolimumab is about 980 mg per week administered intravenously. The same or similar dosing can be used in accordance with various embodiments of the present invention, or an alternate dosage may be used in connection with alternate embodiments of the invention. The actual dosage can depend upon the judgment of the physician, the condition of the patient, and the effectiveness of the therapeutic method based, for example, on the in vitro responsiveness of relevant cultured cells or histocultured tissue sample, or the responses observed in the appropriate animal models.

EXAMPLES

The following examples are offered for illustrative purposes only, and are not intended to limit the scope of the present invention in any way.

Example 1

Experimental Methods

Mice and Tumor Cells

Female C57BL/6J, BALB/c mice and Pmel-1 mice, 6-8 week old, were purchased from Jackson laboratory (Bar Harbor, Me.) and housed under pathogen-free conditions. FoxP3-GFP transgenic mice express Green Fluorescent Protein under the control of the mouse Foxp3 (forkhead box P3) promoter. DEREG (DEpletion of REGulatory T cells) transgenic mice was generated and described by T. S. Lahl K, Loddenkemper C, Drouin C, Freyer J, Amason J, Eberl G, et al. *J Exp Med.* 2007; 204:57-63. All experiments involving animals were in compliance with federal and state standards, which include the federal Animal Welfare Act and the NIH guide for the care and use of laboratory animals.

B16 cells (mouse melanoma cell line) were transduced with human gp100 (human melanoma antigen) (B16-gp100). RENCA is a murine renal cell carcinoma (RCC) cell line. The cells were maintained in DMEM or RPMI 1640 medium supplemented with 10% heat-inactivated fetal bovine serum (FBS; Life Technologies, Grand Island, N.Y.), 2 mmol/L of L-glutamine, 100 units/mL of penicillin, and 100 µg/mL of streptomycin.

Mouse tumors were generated by subcutaneously injecting $2 \times 10^5$ cells into the flank: B16 tumors into C57BL/6 mice and RENCA tumors into Balb/C mice. Tumor diameter was measured with calipers twice a week and tumor volume was calculated (shortest diameter$^2 \times$ longest diameter/2). In the lung metastasis model, tumor cells were injected intravenously through the tail vein. Lung metastases were counted using a dissection microscope.

Antibodies and Reagents

The following monoclonal antibodies (mAb), with or without a fluorescent conjugate, were obtained from Biolegend (San Diego): anti-CD4 (GK 1.5 and RM4-5), anti-CD8 (53-6.7), anti-CD16/CD32(9.3), anti-CD90.1 (OX-7), anti-CD11c (N418), anti-Bcl2 (BCL/10C4), anti-T-bet (4B10), anti-CD62L (MEL-14), anti-CD279 (PD-1,29F.1A12), anti-FoxP3 (FJK-16s), anti-IFN-γ (XMG1.2), anti-IL-2 (JES6.5H4), anti-IL-4 (11B11), IL-17A (eBio1787). Cell-Trace 5- (and 6-)carboxyfluorescein diacetate succinimidyl ester (CFSE) cell proliferation kit was purchased from Molecular Probes (Eugene, Oreg.). Temsirolimus was purchased from LC Laboratory (Woburn, Mass.).

T Cell Enrichment and Treg Sorting

Mouse spleen and lymph nodes were collected and processed into single-cell suspensions. CD8 and CD4 T-cells were negatively enriched using mouse CD8 or CD4 recovery column kits (Cedarlane Labs, Burlington, N.C.). Purity of CD8 and CD4 cells after negative selection was greater than 85%. FoxP3-GFP cells or antibody stained CD4+ CD25+ cells were sorted by MoFlo Cell Sorter (Fort Collins, Colo.).

Preparation of DCs and T Cell Stimulation

D C preparation has been described (Wang Y, Wang X Y, Subjeck J R, Shrikant P A, Kim H L. *Br J Cancer.* 2011; 104:643-52). Briefly, mouse bone marrows were harvested from femurs and tibias and then placed in 12 well plates at a density of $1 \times 10^6$ cells per well with 10% FBS and 10 ng/ml mouse GM-CSF. The cells were fed every 2 days and harvested 7-9 days later. 75-90% of cells were CD11c positive. To prepare DC vaccine for treatment of mice, DCs were pulsed with tumor cell lysate and activated with 10 ug/ml CpG. DCs were subcutaneously injected into mouse. For in vitro activation of Pmel-1 cells, DC was pulsed with 10 ng/ml mouse gp100 peptide (amino acids 25-33, which is presented by H2-Db class I molecules, Alpha Diagnostic International, San Antonio, Tex.) and activated with 10 ug/ml CpG for 2 hours. DC was washed with PBS, and co-cultured with CFSE labeled Pmel-1 cells. Pmel-1 cells proliferation was analyzed by FACscan.

Adoptive Transfer, CD4 Cells Depletion, and mTOR Inhibition

Pmel-1 lymphocytes were isolated from lymph nodes and spleen of naïve Pmel-1 mice. CD8 lymphocytes were enriched by negative selection using Cedarlane purification column. At least 85% of the resulting cells were CD8+. $5 \times 10^5$ cells were transferred into B57BL/6 mice. The day after adoptive transfer, mice received tumor lysate pulsed DC vaccine. To deplete CD4 cells, αCD4 was administered approximately 7 and 9 days later; mice were inject ip with 250 ug of CD4 mAb (clone GK1.5). To deplete CD8 cells, mice received 250 ug of CD8 mAb (clone 2.43). To deplete FoxP3 cells in DEREG mice, 5 µg DT was injected. Flow cytometry was used to confirm depletion of target cells. For mTor inhibitor treatment, 15 µg temsirolimus was injected i.p. each day for 2 weeks. Flow cytometry was used to analyze memory cells and Treg cells.

In Vivo CTL Assay

The in vivo CTL assay has been described (Wang Y, Wang X Y, Subjeck J R, Shrikant P A, Kim H L. *Br J Cancer.* 2011; 104:643-52). Briefly, single-cell suspensions of splenocytes ($1 \times 10^7$ cells/ml) were obtained from naïve mice and pulsed with or without 10 µM peptide in DMEM containing 10% FBS for 30 min at 37° C. Each cell population was then labeled with a different concentration of CFSE (0.5 or 12.5 µM) at $2 \times 10^7$ cells/ml in PBS/0.1% BSA. CFSE labeling was stopped by addition of an equal volume of FBS for 1 min, and washed 3 times with RPMI complete medium. $5 \times 10^6$ cells from each peptide-pulsed or unpulsed population were mixed and injected i.v. into immunized and unimmunized mice. Sixteen hours following transfer, mice were sacrificed, and splenocytes were harvested. Single-cell suspensions of splenocytes were prepared, and analyzed by flow cytometry. Percent-specific-lysis of fluorescent donor splenocytes was calculated as follows: [(number of unpulsed targets×A−number of pulsed targets)/number of unpulsed targets×A]×100, where A=[number of pulsed targets/number of unpulsed targets] in unimmunized recipient mice.

Statistics

Differences in tumor growth were assessed using repeating measure ANOVA. Statistical differences between numbers of lung metastasis, in vivo CTL killing rates and mean percentages from flow cytometry were evaluated by two-tailed student's T test. All statistical analyzes were performed using Stata 8.0 (StataCorp, College Station, Tex.). P values <0.05 were considered significant.

Example 2 mTOR Inhibition Enhances Anti-Tumor Immunity

In animal models, pharmacologic mTOR inhibition can enhance the formation of immune memory, which can help clear infections and decrease tumor growth. This was a surprising finding because mTOR inhibitors are used to suppress the immune system in patients who have had solid organ transplants. Temsirolimus is a rapamycin analog and one of the first mTOR inhibitors approved by the US, Food and Drug Administration (FDA) as a cancer treatment. In our preclinical model, mTOR inhibition with temsirolimus enhanced the antitumor immunity of tumor lysate-pulsed DCs (referred to here as DC vaccine) (FIG. 1a). Temsirolimus can directly inhibit the growth of some tumors, therefore a tumor prevention study was performed to assess the immune effects of temsirolimus. By administering DC vaccine and temsirolimus 13 days prior to tumor challenge, there is no possibility for a direct antitumor effect, and any decrease in tumor growth can be attributed to immune stimulation. Administering DC vaccine alone decreased growth of B16 tumor cells in mice, however, most mice eventually died due to tumor growth. In contrast, the combination of DC vaccine and temsirolimus resulted in 100% survival and completely prevented the growth of B16 tumor cells.

To assess the immune effect of temsirolimus on specific CD8 lymphocytes, Thy1.1 Pmel-1 lymphocytes were adoptively transferred into Thy1.2 B6 mice (FIG. 1b). Pmel-1 transgenic mice carry a rearranged T cell receptor that recognizes a gp100 epitope (amino acids 25-33) presented by H2-Db MHC class I molecules. Lymphocytes were harvested from B6 mice after they were treated with DC vaccine and temsirolimus. Temsirolimus had both immune stimulating and immune suppressing effects when administered with the DC vaccine. Temsirolimus slightly decreased the percent of CD8 cells that were Pmel-1 lymphocytes (p-value 0.08), however, Pmel-1 lymphocytes had increased expression of Eomes, which is an early marker for memory cell formation. Potentially immune suppressive effects included a decrease in Tbet expression in Pmel-1 lymphocytes and increase in Tregs. These observations were largely mirrored by in vitro mixed lymphocyte culture studies (FIG. 1c). In the in vitro studies, temsirolimus significantly decreased the proliferation of Pmel-1 lymphocytes induced by the DC vaccine.

Example 3

CD4 Depletion Enhanced the Antitumor Effect of mTor Inhibition

Figure 2:
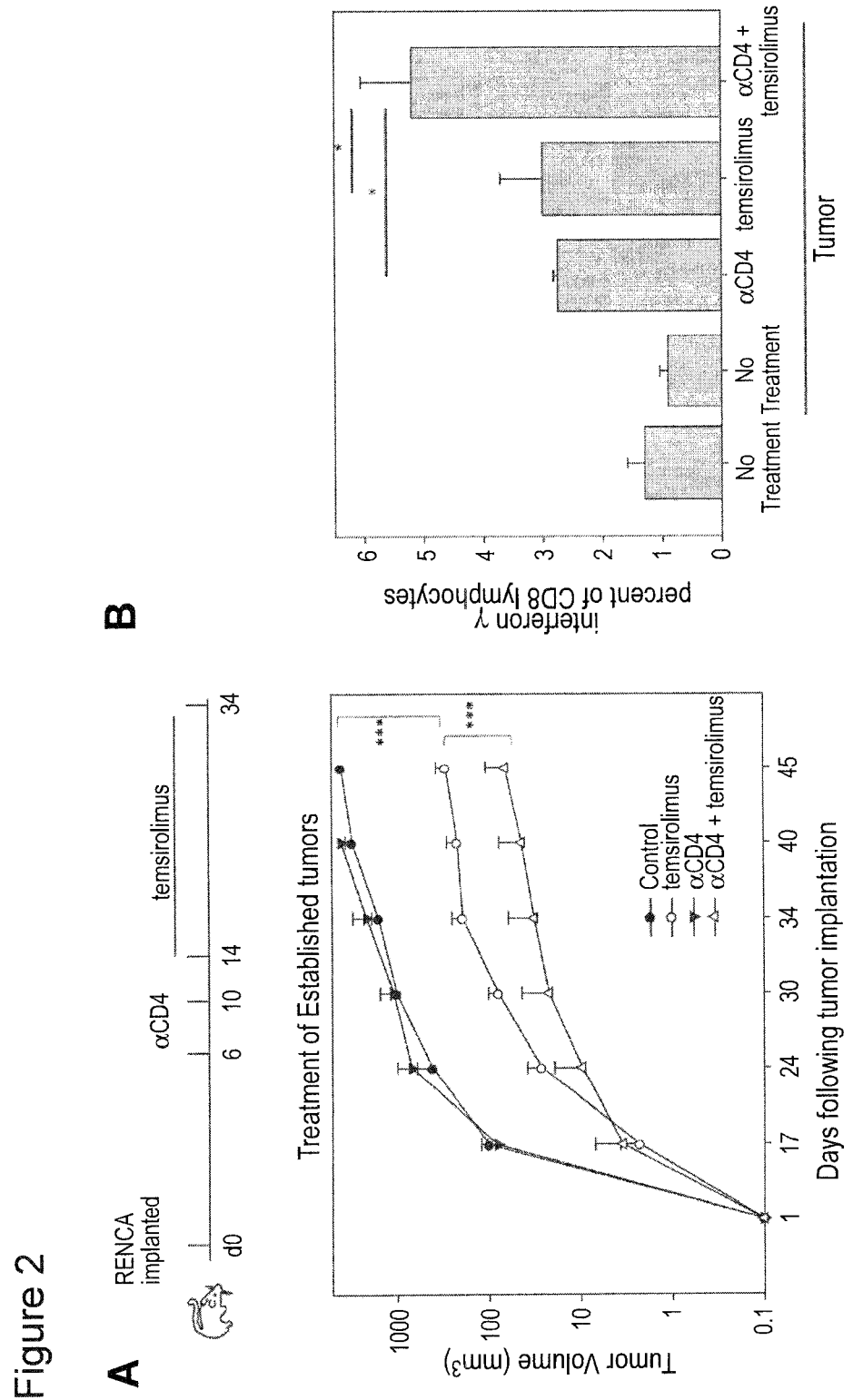
FIG. 2 depicts, in accordance with various embodiments of the invention, that CD4 depletion enhanced the antitumor effect of mTor inhibition. (a) RENCA-CA9 tumor cells were implanted into Balb/C mice (n=5 per group) on day 0. CD4 lymphocytes were depleted with αCD4 antibody on days 6 and 10. Mice were treated with daily temsirolimus on days 14 to 34. Tumor growth was monitored. Results are representative of triplicate experiments. (b) In the same experiment, lymphocytes were harvested on day 45, restimulated with CA9 peptide, and stained for CD8 and IFNγ. (c) Following CD4 depletion, spleen, lymph node and blood were collected on days 0, 1, 10. Lymphocytes were stained for CD4, CD8 and FoxP3 and analyzed by flow cytometry. (c-e) The percentages of CD4 cells in the spleen, lymph node and blood on days 0, 1, and 10 following CD4 depletion are reported. (d) Following CD4 depletion, percentages of splenocytes that are CD4 or CD8 positive are reported, and percent of CD4 cells that are FoxP3 positive is reported. (e) In the same experiment, the absolute numbers of splenocytes positive for CD4, CD8, and CD4/FoxP3 are reported. $*p<0.05$, $p<0.01$, $*p<0.005$.
Figure 2:
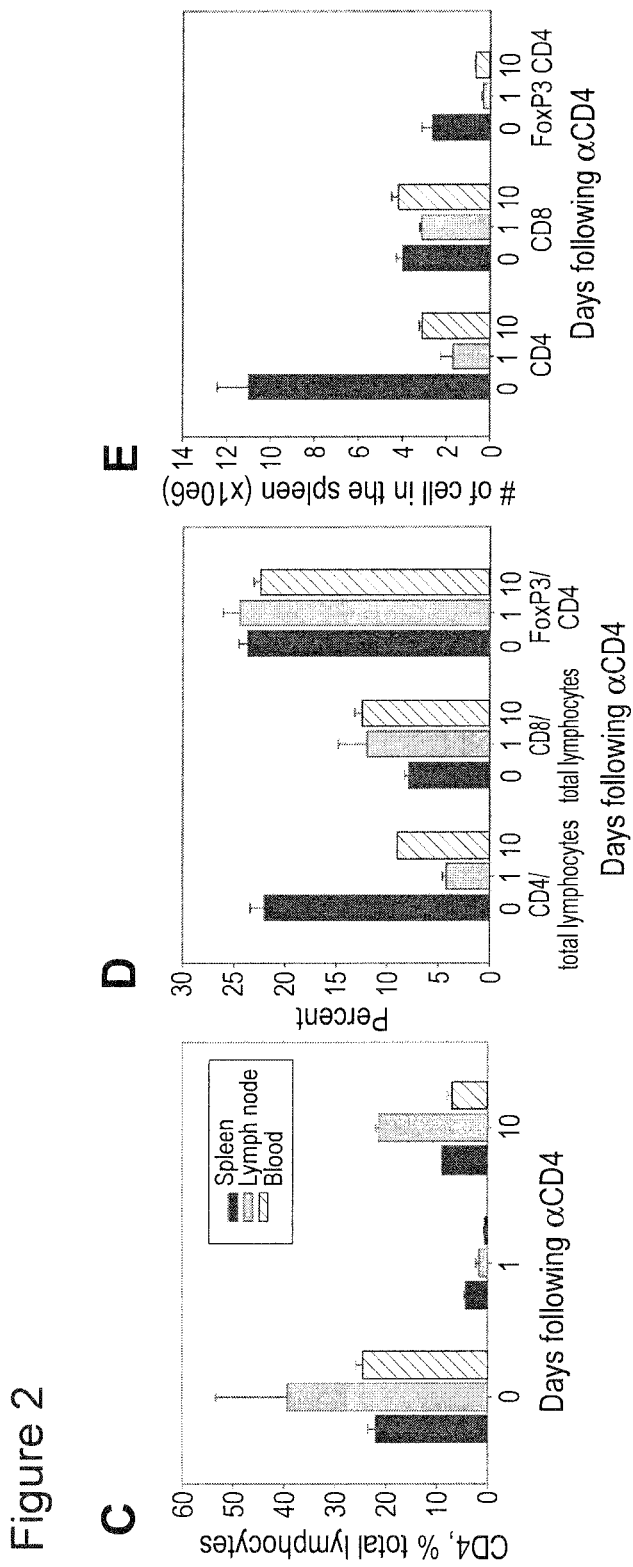
Figure 8:
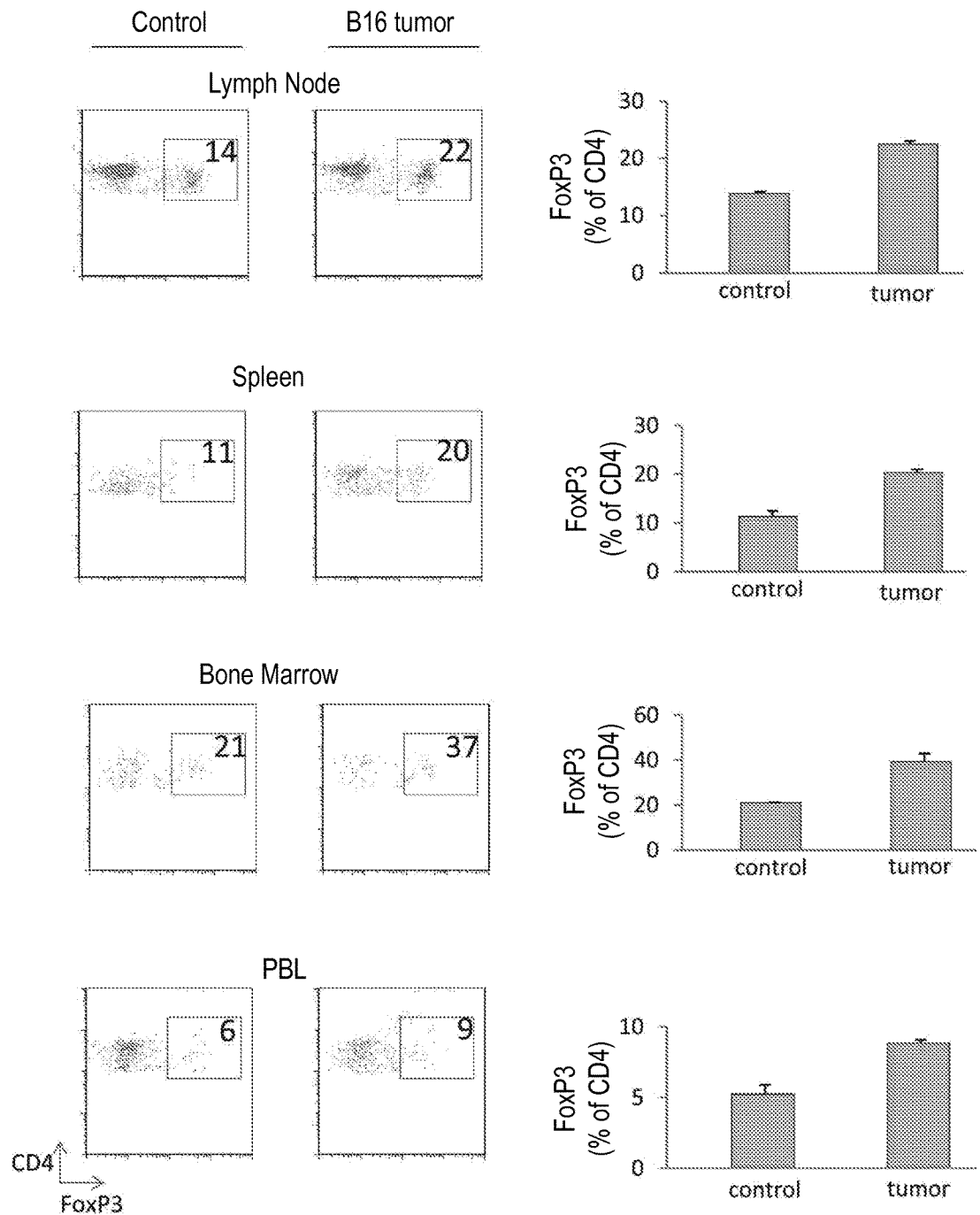
FIG. 8 depicts, in accordance with various embodiments of the invention, that tumor increases Tregs. The percent of CD4 cells expressing FoxP3 were examined from lymph nodes, spleen, bone marrow and peripheral blood lymphocytes (PBL) from tumor bearing mice (~1 cm in diameter) and control mice without tumor. Flow cytometry results are shown.

Temsirolimus produced a net antitumor immune response despite an increase in Tregs. Furthermore, the presence of tumor itself increased Tregs (FIG. 8). Therefore, we hypothesized that the antitumor immunity induced by mTOR inhibition can be further enhanced by targeting Tregs. Currently there is no clinical strategy to selectively remove Tregs; however, it is feasible to deplete all CD4 lymphocytes. However, CD4 effector cells are required for immune activation. Therefore, in our mouse model, CD4 lymphocytes were depleted with αCD4 antibody (αCD4) starting 6 days after immune stimulation by the implanted tumor (FIG. 2). FIG. 1 shows the results in a mouse model of melanoma. We tested this approach in a second model of renal cell carcinoma, another classically immune sensitive tumor. In a tumor treatment model, palpable RENCA tumors were established in Balb/c mice. Temsirolimus has been shown to directly inhibit the growth of RENCA tumor cells in vitro (Wang Y, Wang X Y, Subjeck J R, Shrikant P A, Kim H L. Br J Cancer. 2011; 104:643-52) and was effective in decreasing tumor growth in our mouse model (FIG. 2a). Addition of αCD4 to temsirolimus treatment further decreased tumor growth while αCD4 alone had no effect. It is interesting to note that the combination of αCD4 and temsirolimus decreased tumor growth even when no cancer vaccine was used and the implanted tumor was the only source of specific immune stimulation.

Figure 9:
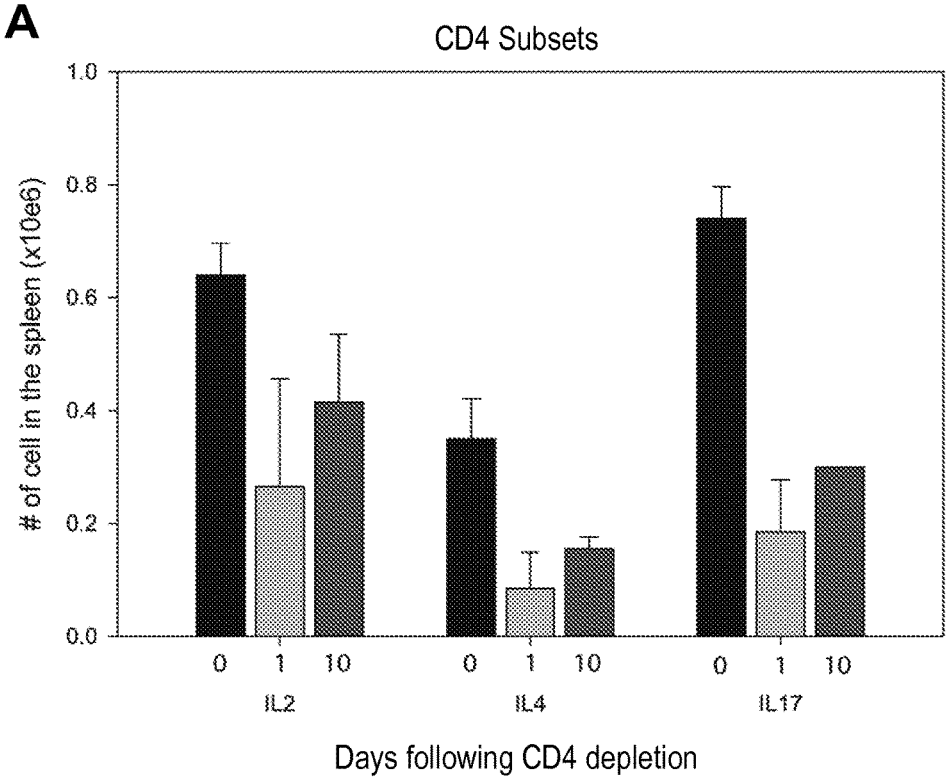
FIG. 9 depicts, in accordance with various embodiments of the invention, that αCD4 antibody depletes effector CD4 subtypes. (a) Splenocytes were collected before (day 0) and 1 or 10 days after administering αCD4 antibody, and analyzed by flow cytometry. The number of total splenocytes staining for CD4 and IL-2, IL-4 or IL-17 is shown. (b) Percent of CD4 cells staining for IL-2, IL-4 or IL-17 is shown.
Figure 9:
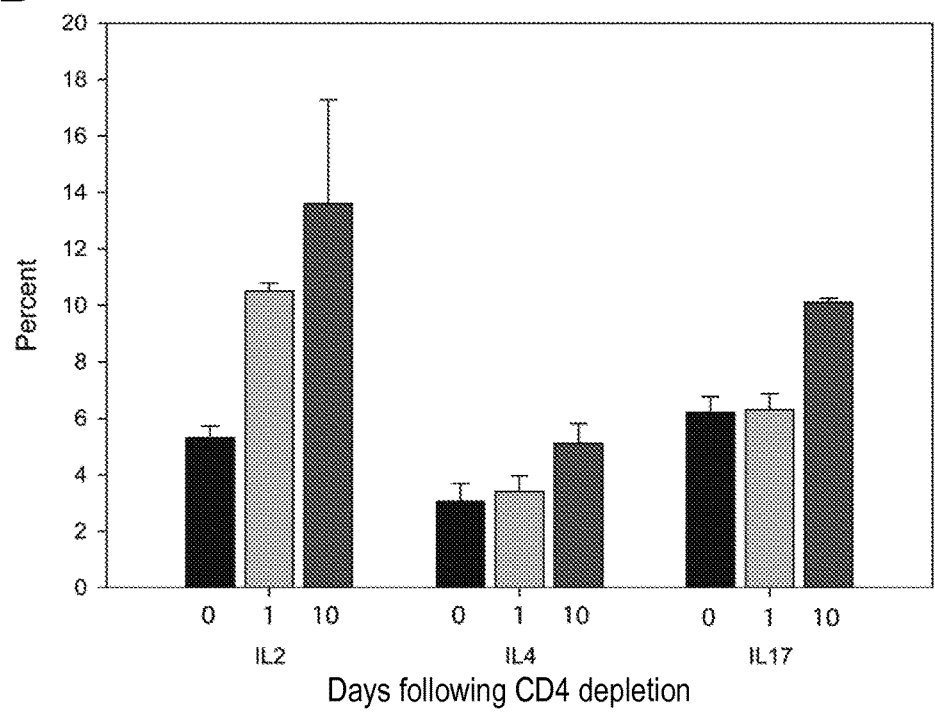

In the same experiment, lymphocytes were harvested on day 45 and assessed for tumor-specific IFN-γ response (FIG. 2b). In tumor-bearing mice that received no treatment, there was no IFN-γ response. Treatment with either αCD4 or temsirolimus produced some IFN-γ response; however, the combination treatment produced the largest IFN-γ response. To characterize the CD4 lymphocyte depletion in response to αCD4, naïve mice were treated with a single dose of αCD4. Nearly all CD4 cells were depleted from the peripheral blood, spleen and lymph nodes by the next day (FIG. 2c) while CD8 cells were preserved (FIG. 2d). Importantly, FoxP3+CD4+ cells were depleted and remained low even 10 days following administration of αCD4 (FIG. 2e). A single dose of αCD4 reduced the population of all CD4 subsets (FIG. 9).

Example 4

Figure 3:
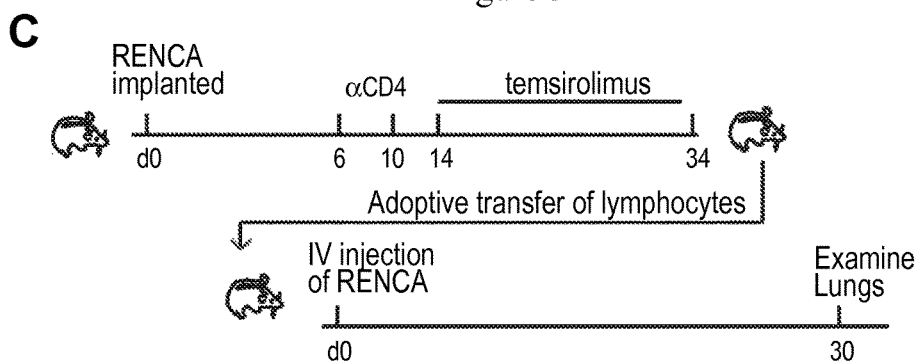
FIG. 3 depicts, in accordance with various embodiments of the invention, that combination of CD4 depletion and temsirolimus generated anti-tumor immunity that was dependent on memory CD8 cells. (a) Tumor-bearing mice (n=8) were treated with daily temsirolimus and then rechallenged with RENCA-CA9 35 days after primary tumor implantation. CD8 cells were depleted by injecting αCD8 antibody on day 36. (b) Tumor-bearing mice (n=8) treated with temsirolimus and CD4 depletion, and then rechallenged with RENCA-CA9 35 days after primary tumor implantation. CD8 cells were depleted by injecting αCD8 antibody on day 36. (c-e) Lymphocytes were harvested from mice treated with temsirolimus and CD4 depletion. The lymphoctes were cultured in vitro with CA9 peptide and IL2 (10 u/ml) for 3 days and then adoptively transferred into naïve B6 mice, which were challenged 24 hrs later with $2 \times 10^5$ RENCA tumor cells injected i.v. Lungs were collected 30 days after the i.v. tumor challenge. Lung weight (d) and number of lung tumor deposits (e) were determined. IL2, interleukin-2, $*p<0.05$, $p<0.01$, $*p<0.005$.
Figure 3:
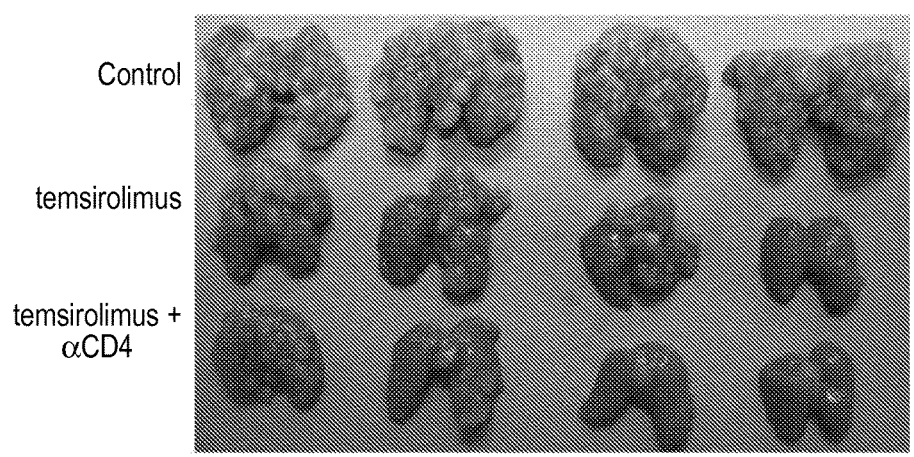
Figure 3:
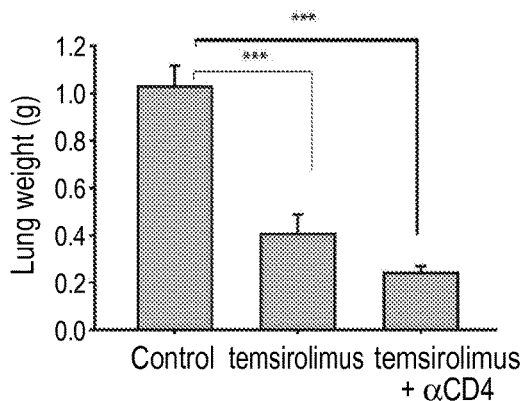
Figure 3:
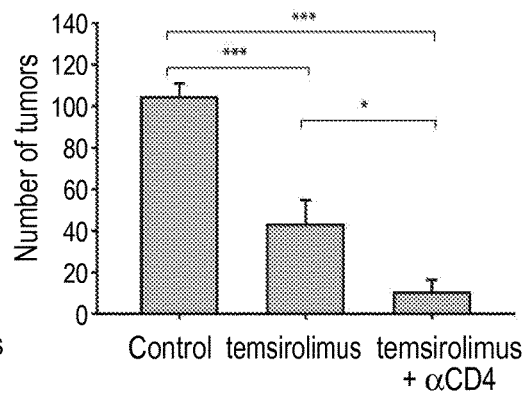

Combination of CD4 Depletion and Temsirolimus Generated Anti-Tumor Immunity that was Dependent on Memory CD8 Cells Since temsirolimus can have a direct antitumor effect, it was important to establish that the combination of αCD4 and temsirolimus was generating an effective antitumor immunity dependent on CD8 lymphocytes. Balb/c mice bearing RENCA tumors were treated with temsirolimus alone for 10 days and then challenged with a second RENCA tumor (FIG. 3a). Mice injected with αCD8 antibody (αCD8) to deplete CD8 effectors cells had increased growth of the second RENCA tumor, indicating that even temsirolimus alone works at least in part by stimulating an immune response. The combination of temsirolimus and αCD4 completely prevented the growth of second RENCA tumors; however, αCD8 removed the antitumor effect on the second tumors, indicating the importance of cellular immunity to tumor control (FIG. 3b).

To further establish the role of the immune system and test our proposed treatment in a more aggressive tumor model, we assessed whether antitumor immunity can be transferred to prevent growth of metastatic lung deposits. The combination of αCD4 and temsirolimus was used to treat established, subcutaneous RENCA tumors (FIG. 3c). Lymphocytes from these mice were adoptively transferred to naïve mice, which were challenged intravenously with RENCA cells. The combination treatment significantly decreased the establishment and growth of lung deposits (FIG. 3c) as quantified by comparing lung weights (FIG. 3d) and counting lung deposits (FIG. 3e). Therefore, memory cells were successfully transferred into naïve mice, where they helped control tumor growth. By depleting CD8 cells, anti-tumor activity was shown to be dependent on CD8 cells. Further confirmation of immune stimulation was provided by transferring CD8 lymphocytes from treated mice to naïve mice. In a very aggressive tumor model, the transferred lymphocytes were effective in controlling growth of metastatic deposits.

Example 5

Figure 4:
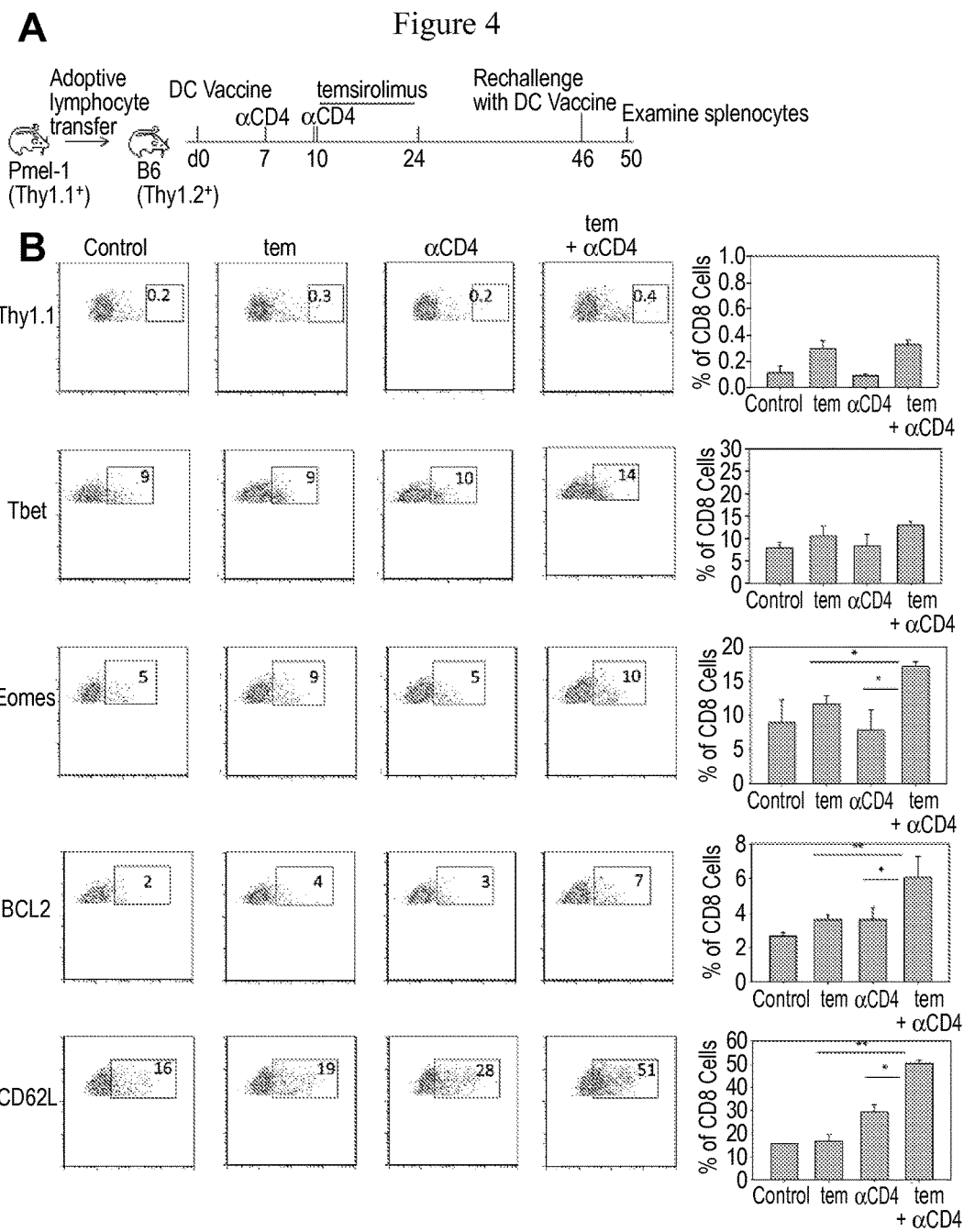
FIG. 4 depicts, in accordance with various embodiments of the invention, that combination of CD4 depletion and temsirolimus treatment enhanced function of CD8 memory cells. (a) Experimental scheme: Lymphocytes from Thy1.1 Pmel-1 mice were adoptively transferred into Thy1.2 B6 mice, which were stimulated with tumor lysate-pulsed DC vaccine and treated with αCD4 antibody on days 7 and 10, and daily temsirolimus on days 10 to 24. Results are representative of triplicate experiments. (b) Splenocytes (n=3 per group) were harvested one day prior to rechallenging with tumor lysate-pulsed DC vaccine, stained with antibodies, and analyzed by flow cytometry. The percent of CD8 cells positive for the indicated marker is shown. (c) Splenocytes (n=3 per group) were harvested 4 days after rechallenging with tumor lysate-pulsed DC vaccine, stained with antibodies, and analyzed by flow cytometry. The percent of CD8 cells positive for the indicated marker is shown. $*p<0.05$, $p<0.01$, $*p<0.005$.
Figure 4:
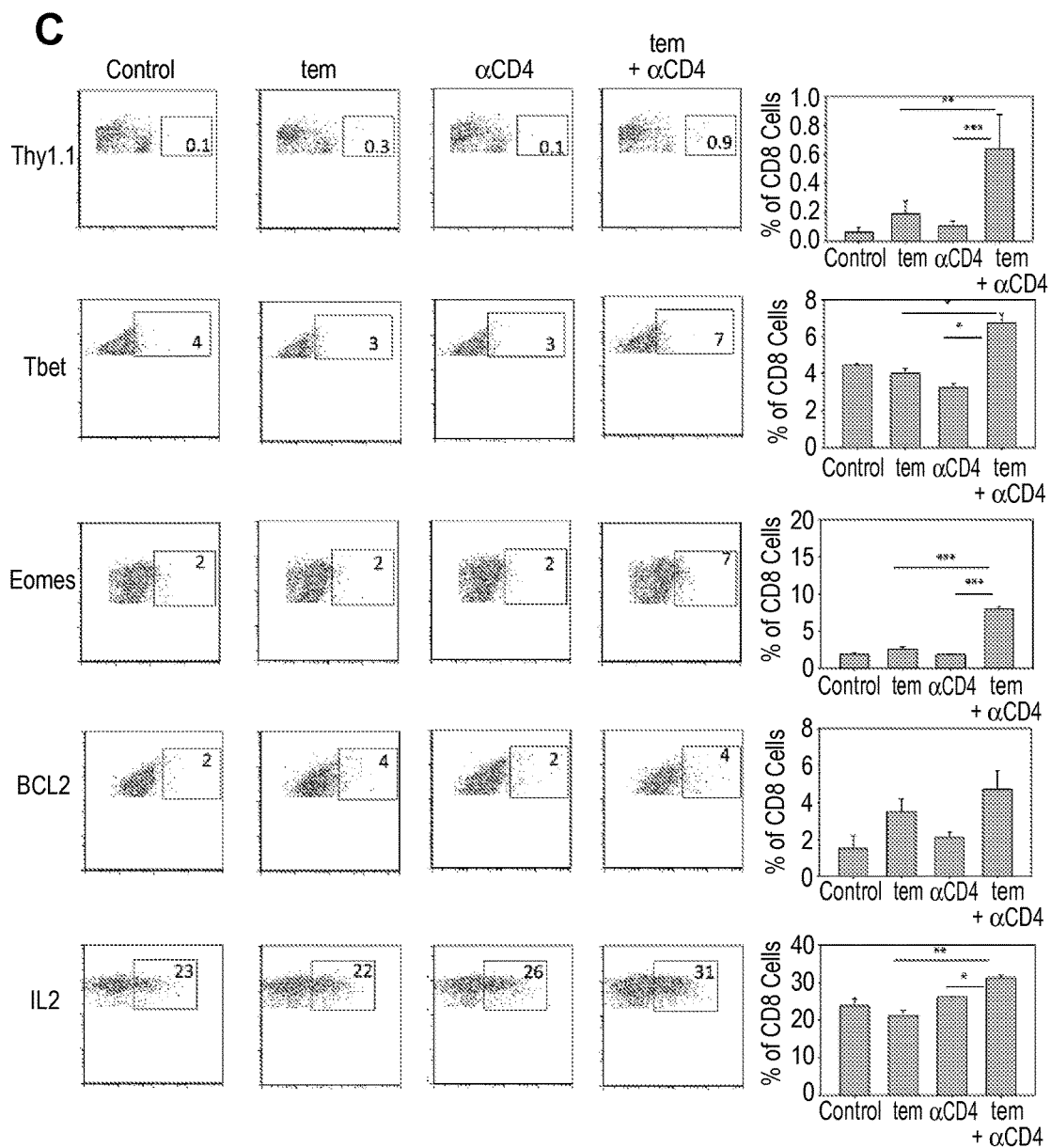

Combination of CD4 Depletion and Temsirolimus Treatment Enhanced Function of CD8 Memory Cells An important mechanism through which temsirolimus inhibits tumor growth is to enhance the quality of specific CD8 memory. Therefore, we characterized the quality of CD8 memory cells with the goal of assessing whether αCD4 further enhances the specific CD8 memory formed in the presence of mTOR inhibition. We used a model where DC vaccines stimulated an immune response rather than the tumor itself since the duration of experiments with tumor-bearing mice is limited by rapid tumor growth in the control groups. By using a DC vaccine, long-term memory can be assessed, including recall responses. Thy1.1 Pmel-1 lymphocytes were adoptively transferred into B6 mice, which were then challenged with B16-DC vaccine and treated with αCD4 and temsirolimus (FIG. 4a).

To assess memory cells, splenocytes were harvest before (FIG. 4b) or after (FIG. 4c) rechallenging mice with DC vaccine on day 46. Immediately prior to rechallenge, there was no significant difference in percent of Pmel-1 lymphocytes in the experimental groups (FIG. 4b). However, the CD8 lymphocytes from mice treated with both αCD4 and temsirolimus had significantly higher expression of memory markers Eomes and BCL2. The CD8 lymphocytes from this group had significantly higher expression of CD62L, which is a marker for highly effective central memory cells. Consistent with high quality memory cells, following rechallenge with DC vaccine, the Pmel-1 cells in the combination treatment group had the greatest expansion and CD8 cells had the highest Tbet and IL2 expression (FIG. 4c). Interestingly, even after rechallenge, the expanded CD8 cells from the combination treatment group had the highest expression of Eomes, an early memory marker. The combination therapy produced CD8 lymphocytes with the strongest memory phenotype capable of rapidly expanding in response to a repeat antigen challenge. In our model, Tregs were present during immune priming since CD4 depletion was initiated at least 6 days after immune stimulation.

Figure 10:
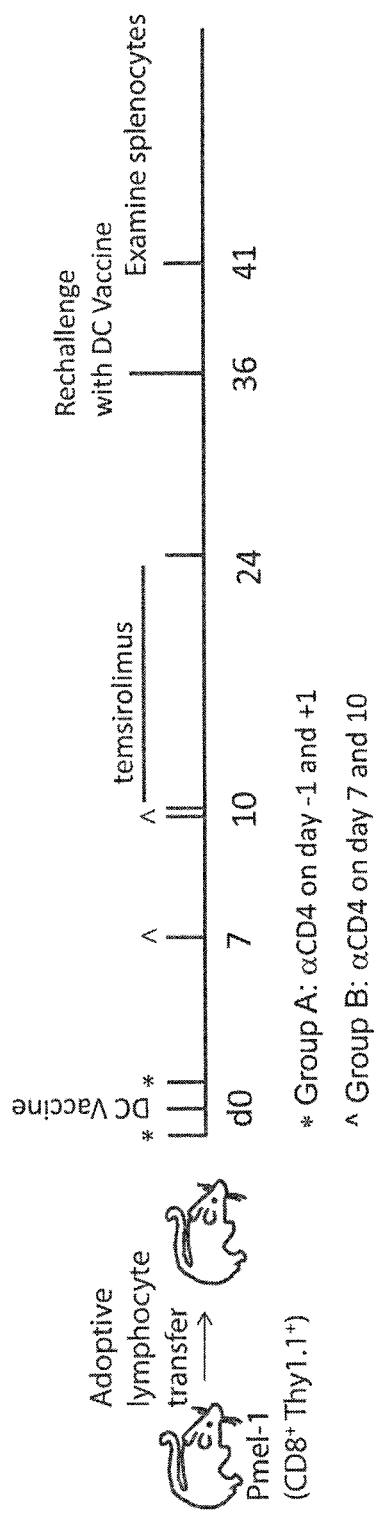
FIG. 10 depicts, in accordance with various embodiments of the invention, that CD4 depletion prior to immune stimulation prevents formation of CD8 memory cells. The experimental scheme is similar to FIG. 4. An additional group is included where αCD4 antibody is administered on day −1 and +1 (Group A). (a) The percent of CD8 cells expressing Thy1.1 is shown from splenocytes harvested 5 days following rechallenge of memory cells. (b) The percent of CD8 cells expressing Eomes is shown. $*p<0.05$, $p<0.01$, $*p<0.005$.
Figure 10:
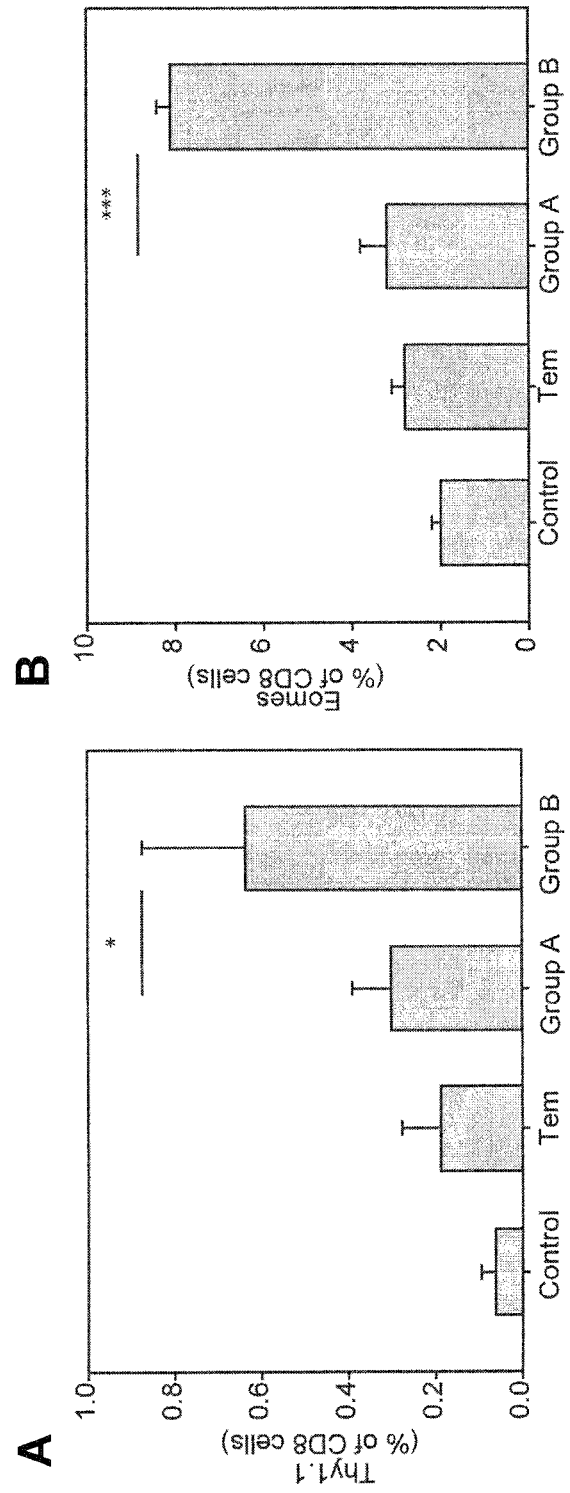

Others have reported that Tregs are necessary, during immune priming, for CD8 memory formation. Therefore, in our treatment models, Tregs were depleted at least 6 days after primary immune stimulation. However, we verified the importance of having CD4 cells during immune priming. When CD4 depletion was performed prior to immune priming, CD8 memory formation was poor, as indicated by a weak tumor-specific CD8 expansion after stimulation of memory cells and low Eomes expression (FIG. 10).

Example 6

Depleting or Replacing Foxp3 Treg Cells Alter CTL Function In Vivo

Figure 5:
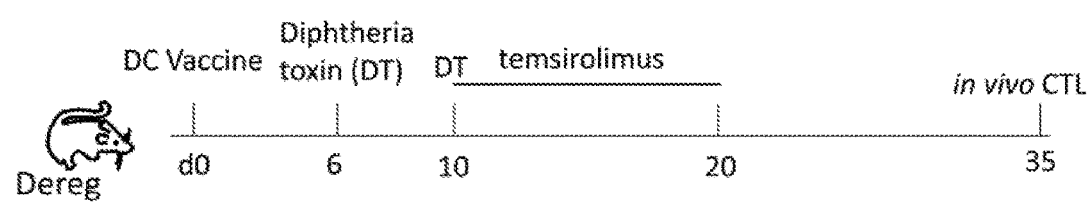
FIG. 5 depicts, in accordance with various embodiments of the invention, that the combination of FoxP3+ Treg depletion and temsirolimus enhanced CTL function in vivo. (a) Experimental scheme: DEREG mice received tumor lysate-pulsed DC vaccine, and were treated intraperitoneally with diphtheria toxin on days 6 and 10, and daily temsirolimus on days 10 to 20. In vivo CTL assay was performed on day 35. (b) CD4+FoxP3+ cells were assessed by flow cytometry using peripheral lymphocytes obtained before and after treating mice with diphtheria toxin. (c) The in vivo CTL results were analyzed by flow cytometry using splenocytes harvested 14 hrs following injection of target cells. CTL, cytotoxic T lymphocyte, $*p<0.05$, $p<0.01$, $*p<0.005$.
Figure 5:
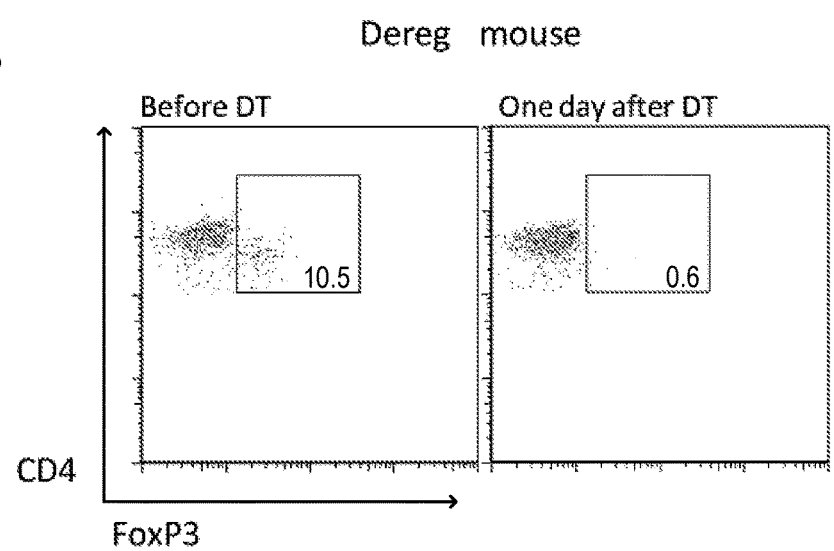
Figure 5:
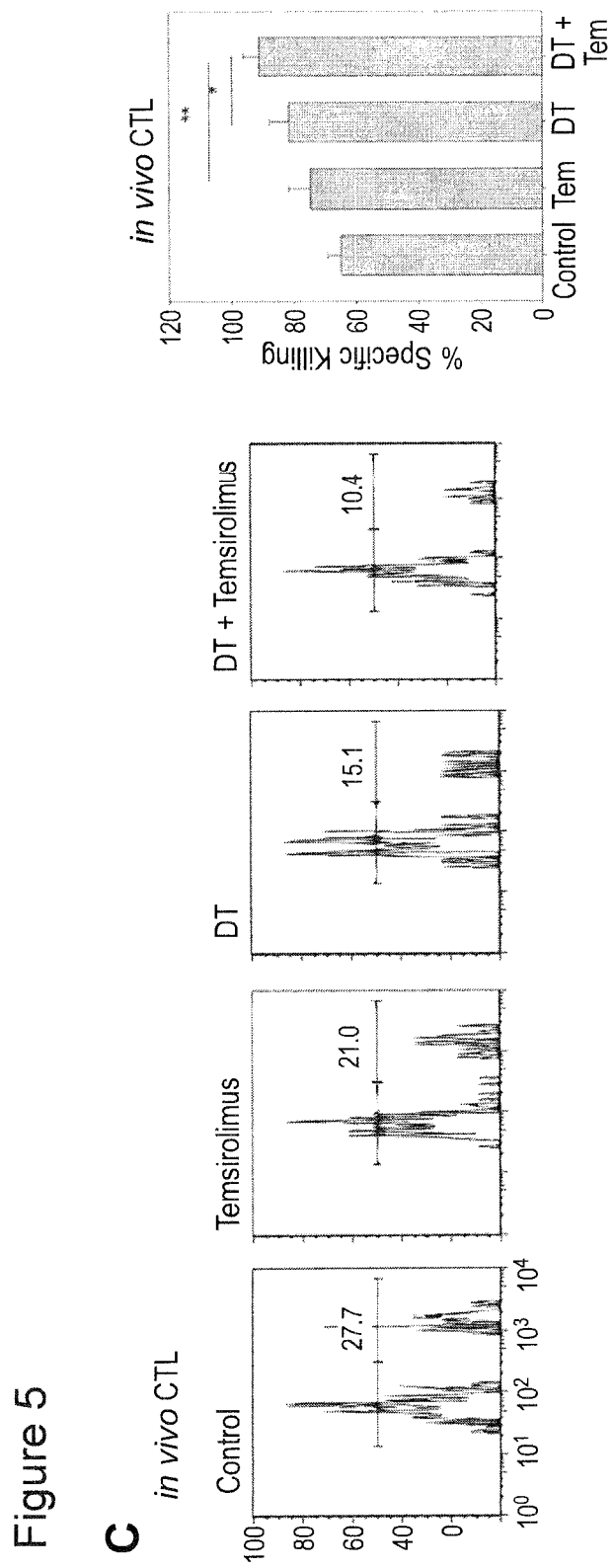

Our original hypothesis was that depletion of Tregs normally induced by temsirolimus will enhance antitumor immunity. We selected CD4 depletion as a strategy for depleting Tregs since CD4 depletion is feasible in patients. However, we wanted to test whether the effect of CD4 depletion can be directly attributed to Tregs depletion. Therefore we used DEREG (DEpletion of REGulatory T cells) transgenic mice, which carry a DTR-eGFP transgene under the control of Foxp3 promoter, allowing specific depletion of Tregs by administering diphtheria toxin (DT) (Lahl K, Loddenkemper C, Drouin C, Freyer J, Amason J, Eberl G, et al. *J Exp Med.* 2007; 204:57-63.). In an experiment analogous to one shown in FIG. 2, DT was administered on days 6 and 10, in place of αCD4 (FIG. 5a). The immune system was stimulated with DC vaccine and specific immune memory was assessed on day 35 by in vivo CTL (FIG. 5c). DT administration removed nearly all CD4+ FoxP3+ lymphocytes (FIG. 5b). Specific killing significantly increased in mice treated with DT and temsirolimus when compared to control groups (FIG. 5c, right most panel). Therefore, removing Tregs had a similar immune effect to CD4 depletion.

Figure 6:
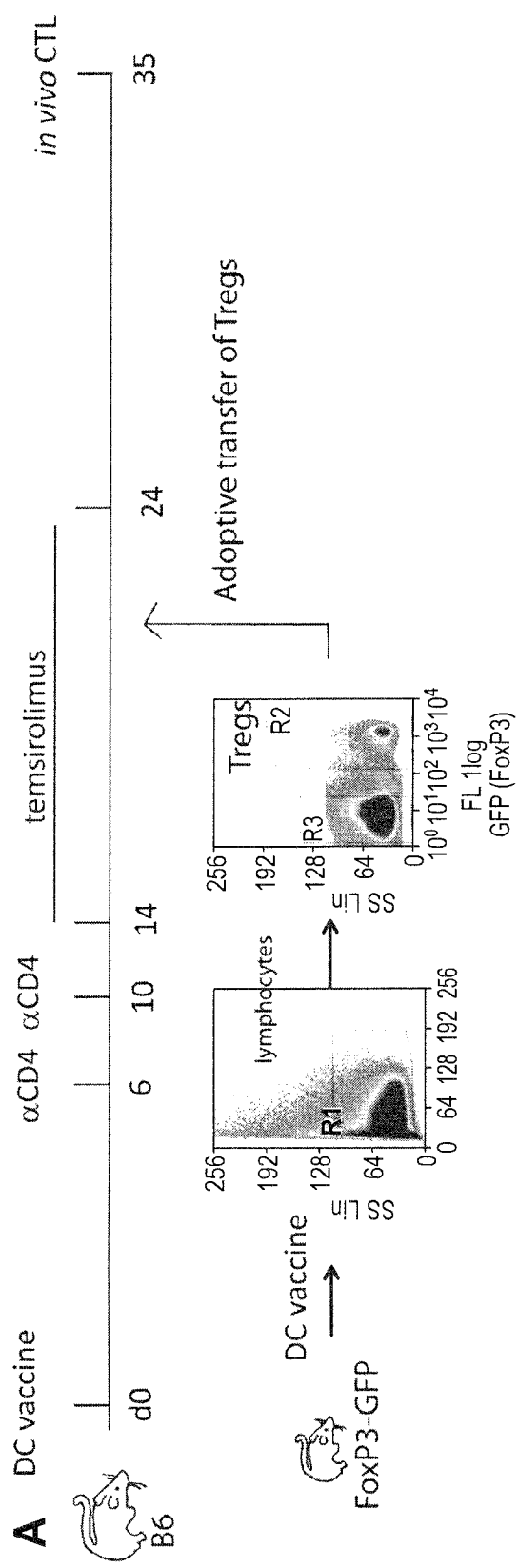
FIG. 6 depicts, in accordance with various embodiments of the invention, that adoptive transfer of FoxP3+ Tregs reduced CTL function in vivo in mice treated with the combination of CD4 depletion and temsirolimus. (a) Experimental scheme: B6 received tumor lysate-pulsed DC vaccine, and were treated intraperitoneally with αCD4 antibody on days 6 and 10, and daily temsirolimus on days 14 to 24. Tregs, sorted from lymphocytes from GFP-FoxP3 mice that received tumor lysate-pulsed DC vaccine, were adoptively transferred on day 20 and in vivo CTL assay was performed on day 35. (b) The in vivo CTL results were analyzed by flow cytometry using splenocytes harvested 14 hrs following injection of target cells (n=3 per group). $*p<0.05$, $p<0.01$, $*p<0.005$.
Figure 6:
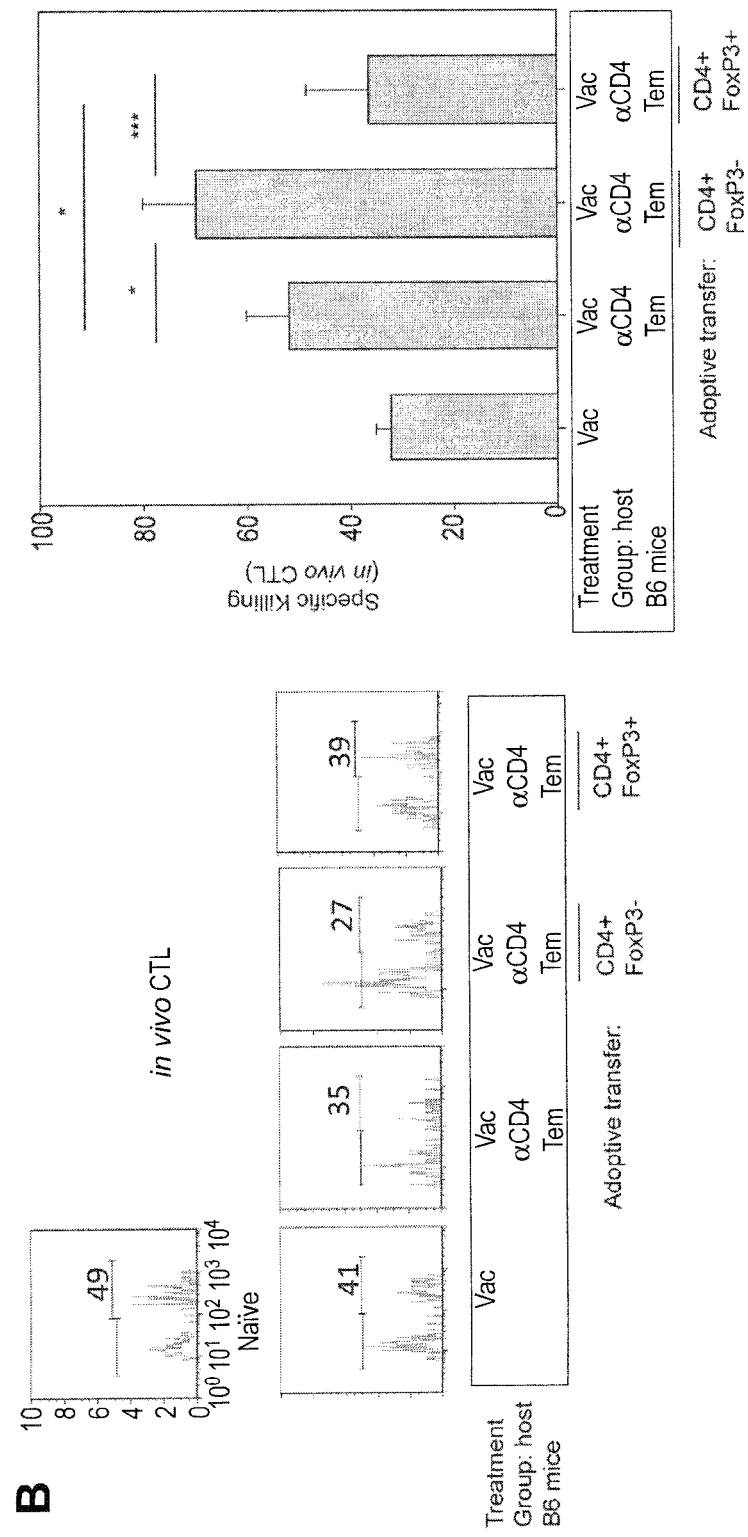

To fully establish Treg depletion as the underlying mechanism for immune stimulation following CD4 depletion, Tregs were replaced after CD4 depletion (FIG. 6a). Mice treated with αCD4 and temsirolimus developed the best specific immune memory as assessed by in vivo CTL (FIG. 6b). However, when Tregs from mice treated with DC vaccine were adoptively transferred, specific killing decreased to that of control mice that only received the DC vaccine (FIG. 6b, right most panel). These experiments confirm that with αCD4 it is the Treg depletion that enhances specific immune memory formation.

Example 7

Figure 7:
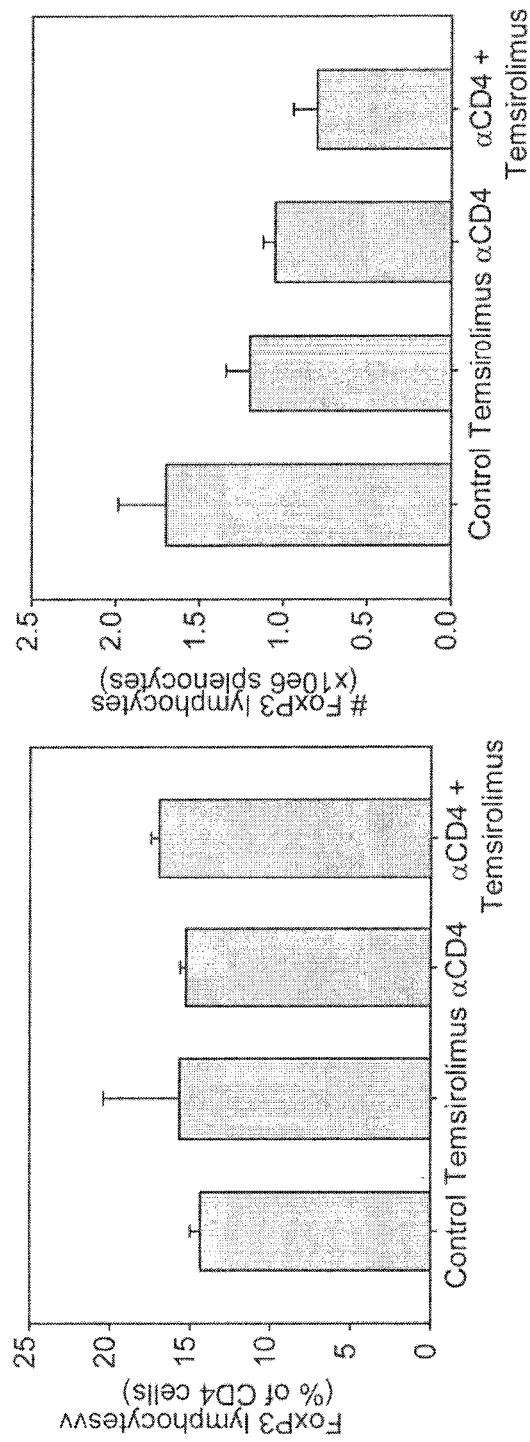
FIG. 7 depicts, in accordance with various embodiments of the invention, that after treatment with CD4 depletion, Treg population that recovers is less immunosuppressive. (a) Mice were treated using the experimental scheme outlined in FIG. 4a. On day 45, splenocytes were examined by flow cytometry for CD4+FoxP3+ cells. (b) The splenocytes that recovered after CD4 depletion were used to enrich for CD4+ cells, which were then sorted by CD25 status. For the resulting groups, representative flow cytometry for CD4+ CD25+ status and CD4+CD25− status are shown. (c) CD4+ CD25− cells were co-cultured with DCs pulsed with B16 tumor lysate. The CD4+CD25− cells were analyzed by flow cytometry for IFNγ or IL4 expression. (d) CD4+CD25+ cells were co-cultured with DCs pulsed with B16 tumor lysate and CD8 cells from mice immunized with DCs pulsed with B16 tumor lysate. CD8 cell proliferation was monitored by flow cytometry using a CFSE dilution assay. $*p<0.05$, $p<0.01$, $*p<0.005$.
Figure 7:
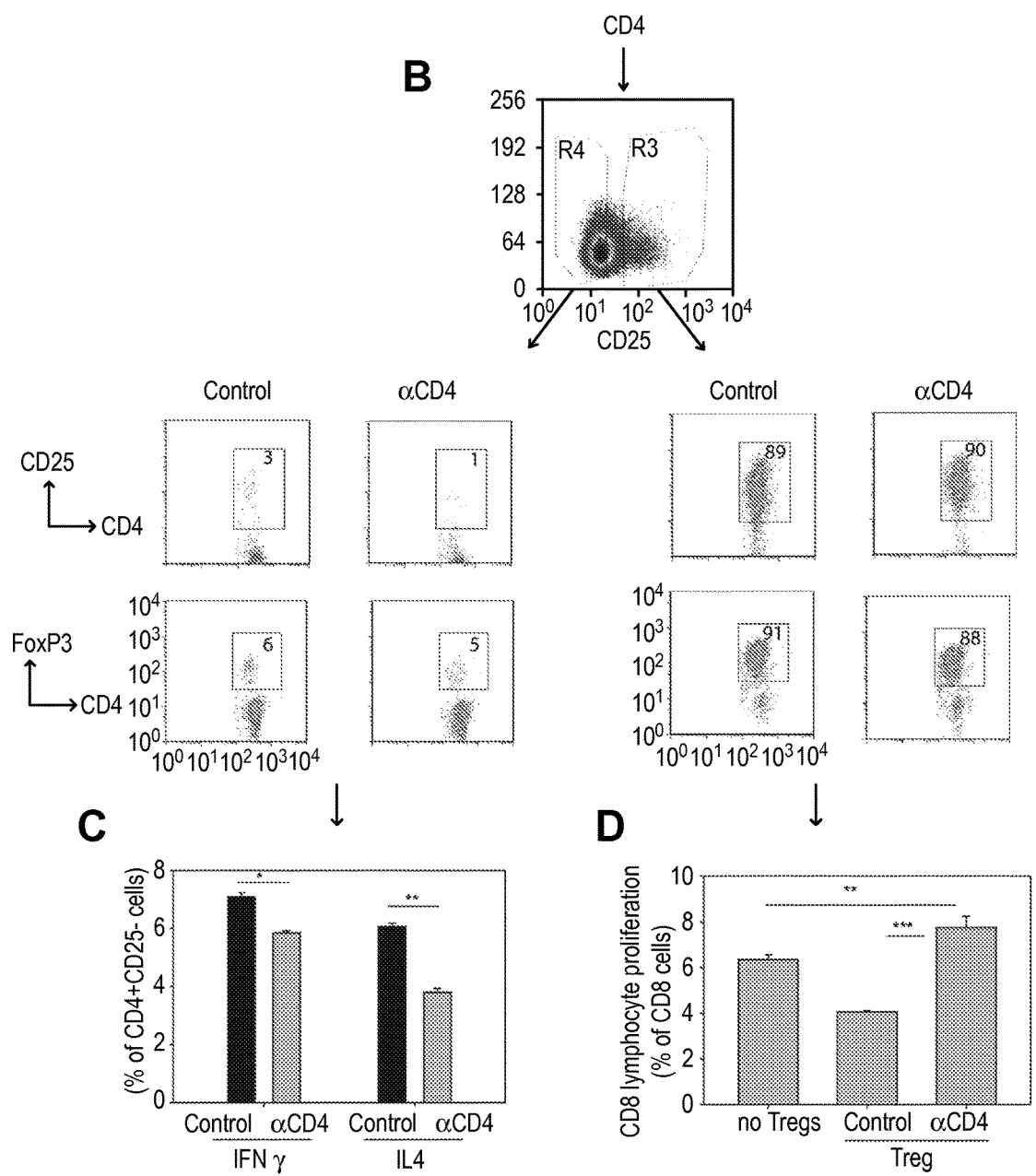

Following CD4 Depletion, Treg Population that Eventually Recovers is Less Immunosuppressive Following treatment with DC vaccine, αCD4, and temsirolimus, the Treg population eventually recovers (FIG. 7a). Between experimental groups, the differences in absolute number of Tregs in the spleen were not statistically significant. However, the treatments may have had a long-term effect on Treg function. Therefore, we assessed the immunosuppressive function of the recovered Tregs. CD4 lymphocytes were sorted based on CD25 status (FIG. 7b). The vast majority of the CD4+CD25+ cells were FoxP3 positive and were considered Tregs, and the vast majority of CD4+CD25− cells were FoxP3 negative and were considered CD4 effector cells. In functional studies, control CD4+ CD25+ cells suppressed the proliferation of CD8 lymphocytes. However, CD4+CD25+ that recovered after CD4 depletion were less immunosuppressive, possibly because they were less likely to be tumor-specific Tregs (FIG. 7d). Interestingly, following CD4 depletion, the recovered CD4 effector cells were also less effective as indicated by lower IFNγ and IL4 secretion (FIG. 7c). It is possible that both CD4 effector cells and Tregs were less likely to be tumor-specific.

Immunotherapeutic approaches have proven effective for the treatment of solid tumors. The FDA approved sipuleucel-T, which became the first commercially available cancer vaccine for the treatment of a solid tumor. Ipilimumab, a monoclonal antibody targeting CTLA4, was more recently approved for the treatment of melanoma. Immune checkpoint inhibitors that target CTLA4 and PD-1 are being actively investigated in a large number of clinical trials for various malignancies. There have always been hints that immune-based therapies can even be curative in subsets of patients with metastatic disease, but recent advances in immunotherapy reaffirm that durable complete responses are possible. Therefore, immunotherapy is one of the most promising approaches to cancer therapy.

Example 8

Figure 11:
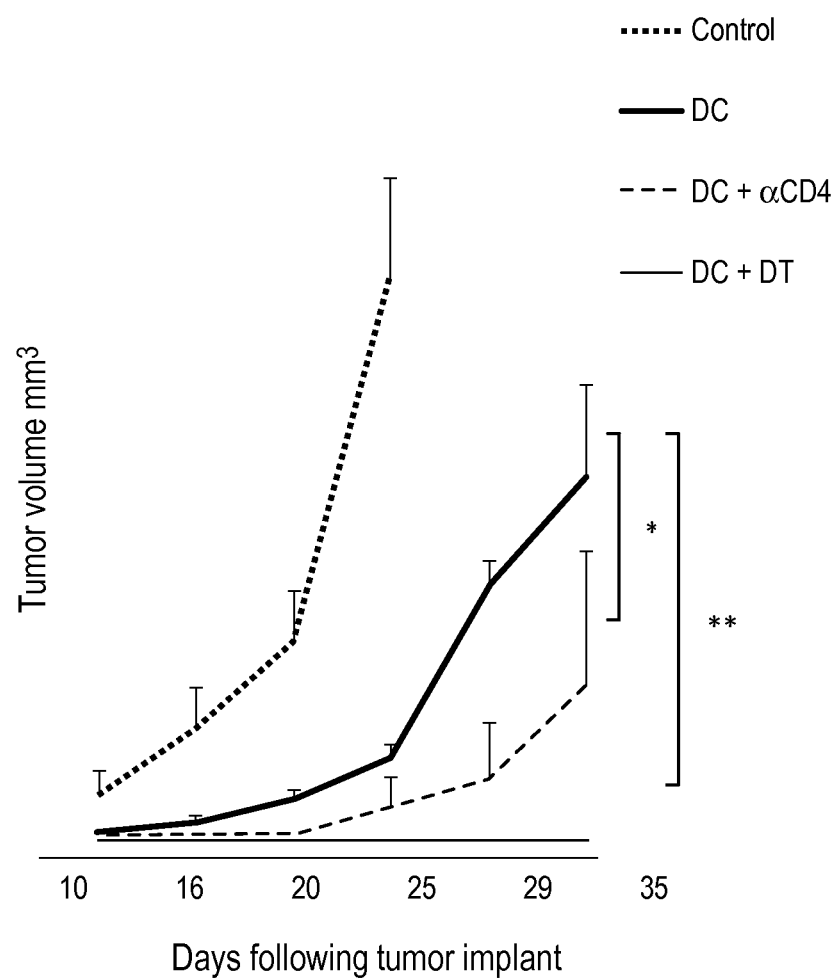
FIG. 11 depicts, in accordance with various embodiments of the invention, that Depletion of Tregs or CD4 cells enhance antitumor effect.

Combination of CD4 Lymphocyte Depleting Agent and Adoptive Immune Therapeutic Agent Enhances Antitumor Affect B16 tumor cells were implanted into DREG mice, which are B6 mice engineered to express the diphtheria toxin receptor behind the FoxP3 promoter. Mice received tumor lyate-pulsed DC vaccine on day 2. Tregs were specifically depleted with diphtheria toxin and CD4 cells were removed with αCD4 antibody on day 6 and 10. Tumor growth was monitored. * p=0.05, ** p=0.0009. As shown in FIG. 11, combination of CD4 lymphocyte depletion and a DC vaccine enhances the antitumor effect when compared to DC vaccine alone.

Example 9

Figure 12:
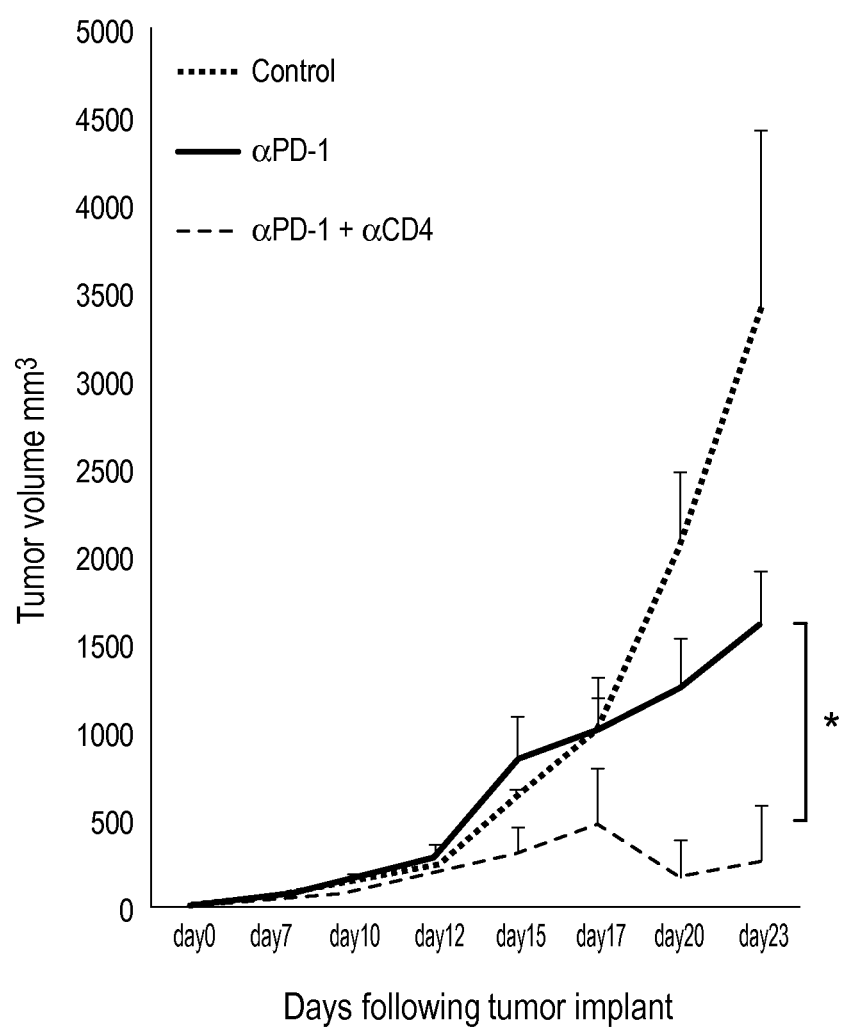
FIG. 12 depicts, in accordance with various embodiments of the invention, that CD4 depletion enhances PD-1 blockade antitumor effect.

Combination of CD4 Lymphocyte Depleting Agent and Immune Checkpoint Inhibitor Enhances Antitumor Affect B16 tumor cells were implanted into B6 mice. On day 0. CD4 cells were depleted with αCD4 antibody on day 6 and 10. Mice were treated with αPD-1 antibody on day 10 to 24. Tumor growth was monitored. * p=0.02. As shown in FIG. 12, combination of CD4 lymphocyte depletion and anti-PD-1 antibody enhances antitumor effect when compared to anti-PD-1 antibody alone.

Example 10

Anti-CD4 Antibody Exhibits Anti-Tumor Activity

Figure 13:
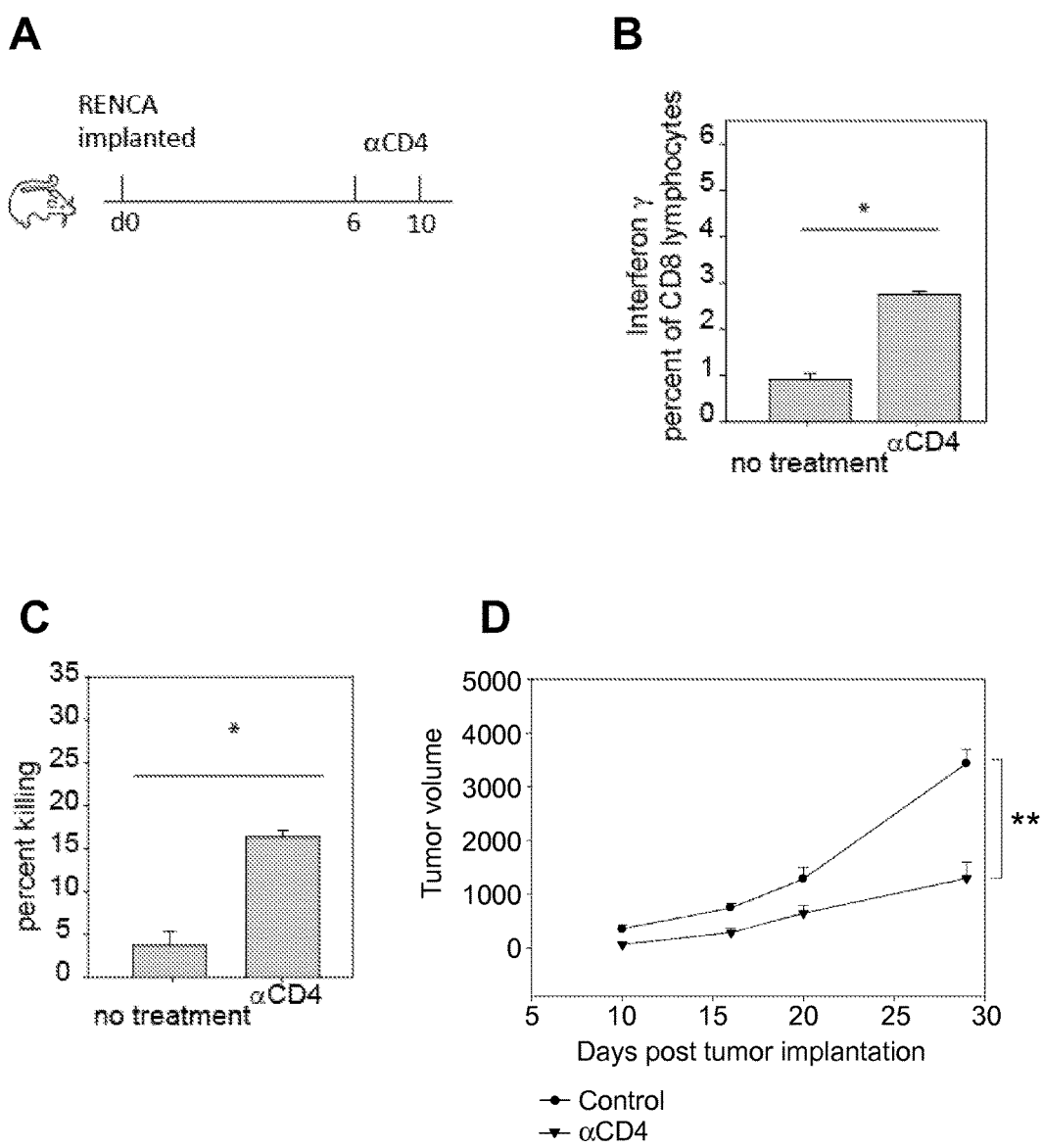
FIG. 13 depicts, in accordance with various embodiments of the invention, that CD4 depletion enhances to tumor-specific cellular immunity. A. Experimental schematic. B. CD4 depletion stimulated tumor-specific interferon-gamma secretion from CD8 cells. Therefore, CD4 depletion led to educating of CD8 cells that were capable of being activated in response to tumor. C. These same CD8 cells were capable of killing RENCA tumor cells. D. B16 tumor growth curve.

RENCA-CA9 tumor cells were implanted into Balb/C mice (n=5 per group) on day 0. CD4 lymphocytes were depleted with αCD4 antibody on days 6 and 10 (FIG. 13A). Lymphocytes were harvested on day 45, restimulated with CA9 peptide, and stained for CD8 and IFNγ. Results are representative of duplicate experiments (FIG. 13B). For the in vitro CTL assay, splenocytes were harvest on day 45 and cultured with IL2, RENCA lysate and CA9 peptide. Target cells were prepared by labeling RENCA cells with CFSE. Effector and target cells were co-cultured at a ratio of 50:1 and analyzed by FACS for the percent of CFSE+ cells that were 7-AAD positive and annexin V negative (FIG. 13C). Histograms provide mean+SEM. *p<0.05. B16 tumor growth curve shows that anti-CD4 antibody has anti-tumor effect (FIG. 13D). As shown in FIG. 13, CD4 depletion produces tumor-specific CD8 cells capable of activating and tumor cell killing in the presence of tumor antigen.

Example 11

Figure 14:
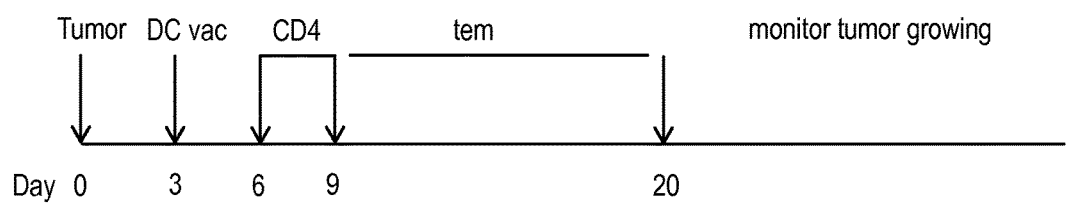
FIG. 14 depicts, in accordance with various embodiments of the invention, that combination of anti-CD4 antibody, Temsirolimus and dendritic cell vaccine exhibited enhanced anti-tumor activity. A. Experimental schematic. B. B16 tumor growth curves are shown with standard error of mean (SEM). $**p<0.001$.
Figure 14:
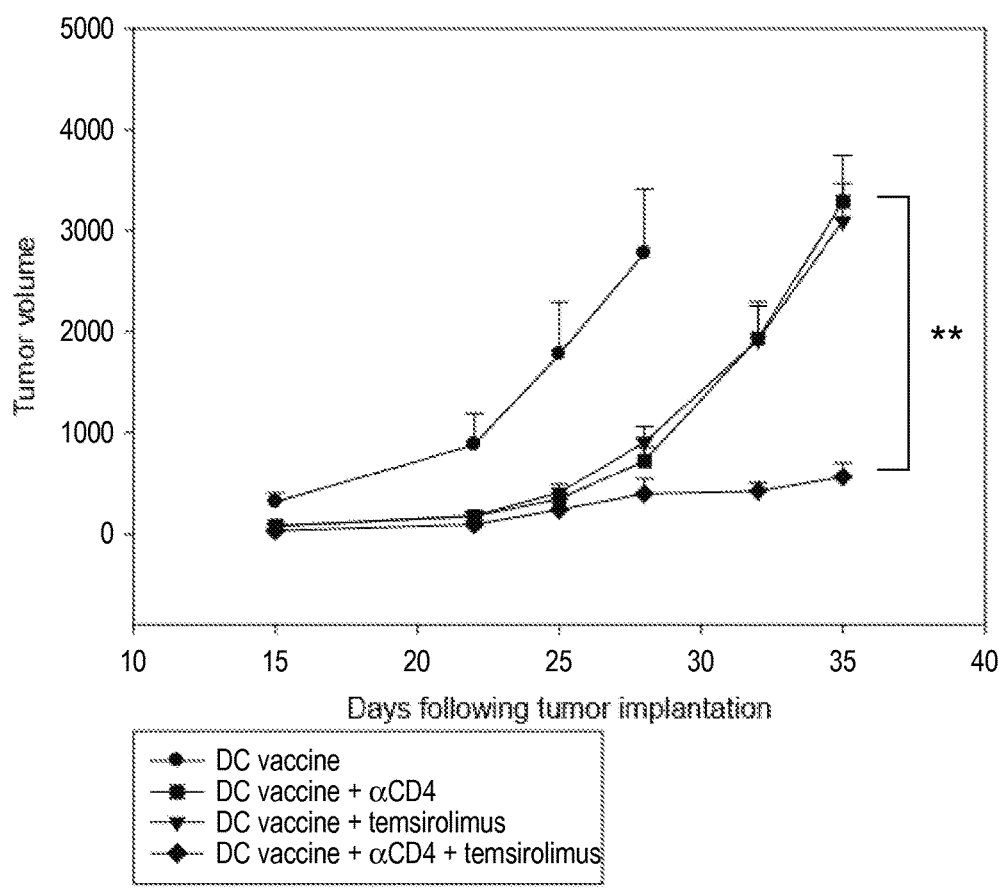

Combination of CD4 Lymphocyte Depleting Agent, Adoptive Immune Therapeutic Agent and mTOR Inhibitor Enhances Anti-Tumor Affect B16 tumor cells were injected subcutaneously in the flank of B6 mice (n=5 per group) on day 0. Mice received tumor lysate-pulsed DC vaccine on days 3 and CD4 lymphocyte depletion (using anti-CD4 antibody) was performed on days 6 and 9. Temsirolimus was injected intraperitoneally daily on days 9 to 20. B16 tumor growth curves are shown with SEM. **p<0.001. As shown in FIG. 14, the combination of CD4 lymphocyte depleting agent, dendritic cell vaccine and mTOR inhibitor (temsirolimus) effectively controlled growth of tumors.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

What is claimed is:

1. A method of treating, reducing the severity of and/or slowing the progression of cancer in a subject in need thereof, comprising:
   administering to the subject a therapeutically effective amount of an anti-CD4 antibody to deplete CD4+ regulatory T cells (Tregs) after the cancer has primed the subject's immune system to stimulate an immune response; and
   administering a therapeutically effective amount of an immune checkpoint inhibitor to the subject, thereby treating, reducing the severity of and/or slowing the progression of the cancer in the subject, wherein the immune checkpoint inhibitor is selected from the group consisting of an antibody against PD-1, an antibody against PD-L1, or a combination thereof,
   wherein the administration of the anti-CD4 antibody induces interferon-gamma (IFN-γ) response in the subject, and
   wherein the cancer is melanoma, breast cancer, colon cancer, or a combination thereof.

2. The method of claim 1, wherein the subject is a human.

3. The method of claim 1, wherein the anti-CD4 antibody is a monoclonal antibody or an antigen binding fragment thereof, a polyclonal antibody or an antigen binding fragment thereof, a chimeric antibody, a humanized antibody, a human antibody or an antigen binding fragment thereof, or a single chain antibody.

4. The method of claim 1, wherein the anti-CD4 antibody is a humanized anti-CD4 antibody.

5. The method of claim 1, wherein the anti-CD4 antibody is zanolimumab.

6. The method of claim 1, wherein the anti-CD4 antibody is administered at 100-200 mg/day, 200-300 mg/day, 300-400mg/day, 400-500 mg/day, 500-600 mg/day, 600-700 mg/day, 700-800 mg/day, 800-900 mg/day, 900-1000mg/day, 1000-1100 mg/day, 1100-1200 mg/day, 1200-1300 mg/day, 1300-1400 mg/day, 1400-1500 mg/day, 1500-1600 mg/day, 1600-1700 mg/day, 1700-1800 mg/day, 1800-1900 mg/day or 1900-2000 mg/day.

7. The method of claim 1, wherein the anti-CD4 antibody and the immune checkpoint inhibitor are administered intravenously, or intraperitoneally.

8. The method of claim 1, wherein the anti-CD4 antibody and the immune checkpoint inhibitor are administered concurrently.

9. The method of claim 1, wherein the anti-CD4 antibody is administered before administering the immune checkpoint inhibitor.

10. The method of claim 1, wherein the immune checkpoint inhibitor is administered at 0.1-0.5 mg/day, 0.5-1.0 mg/day, 1.0-1.5 mg/day, 1.5-2.0 mg/day, 2.0-2.5 mg/day, 2.5-5 mg/day, 5-10 mg/day, 10-15 mg/day, 15-20 mg/day, 20-25 mg/day, 25-30 mg/day, 30-35 mg/day, 35-4 0mg/day, 40-45 mg/day, 45-50 mg/day, 50-55 mg/day, 55-60 mg/day, 60-65 mg/day, 65-70 mg/day, 70-75 mg/day, 75-80 mg/day, 80-85 mg/day, 85-90 mg/day, 90-95 mg/day or 95-100 mg/day.

11. The method of claim 1, further comprising administering an effective amount of an immune adjuvant.

12. The method of claim 11, wherein the immune adjuvant is selected from the group consisting of an aluminum salt, a virosome, an oil-based adjuvant, and a combination thereof.

13. The method of claim 1, further comprising administering to the subject a therapeutically effective amount of an immune modulating agent.

14. The method of claim 13, wherein the immune modulating agent is an mTOR inhibitor.

15. The method of claim 14, wherein the mTOR inhibitor is selected from the group consisting of (i) temsirolimus (CCI-779), (ii) evirolimus (RAD-001), and (iii) sirolimus (rapamycin).

16. The method of claim 1, further comprising administering a therapeutically effective amount of an adoptive immune therapeutic agent.

17. The method of claim 16, wherein the adoptive immune therapeutic agent is a dendritic cell vaccine.

18. The method of claim 16, wherein the adoptive immune therapeutic agent is selected from the group consisting of a dendritic cell vaccine, a peptide vaccine, an immune cytokine, a heat shock protein-based vaccine, a tumor lysate-based vaccine, and a viral vector carrying a tumor antigen.

* * * * *